(12) United States Patent
Giersch et al.

(10) Patent No.: US 9,308,004 B2
(45) Date of Patent: Apr. 12, 2016

(54) DISTAL TARGETING DEVICE

(71) Applicant: Stryker Trauma GmbH, Schoenkirchen (DE)

(72) Inventors: Helge Giersch, Laboe (DE); Klaus Dorawa, Schoenkirchen (DE); Bernd Simon, Kiel (DE); Stefan Völzow, Moenkeberg (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 265 days.

(21) Appl. No.: 14/159,678

(22) Filed: Jan. 21, 2014

(65) Prior Publication Data

US 2014/0163571 A1 Jun. 12, 2014

Related U.S. Application Data

(60) Division of application No. 11/891,287, filed on Aug. 9, 2007, which is a continuation-in-part of application No. 11/593,996, filed on Nov. 7, 2006, now Pat. No. 8,685,034.

(60) Provisional application No. 60/836,793, filed on Aug. 10, 2006.

(51) Int. Cl.
*A61B 17/17* (2006.01)
*A61B 17/72* (2006.01)

(52) U.S. Cl.
CPC ......... *A61B 17/1703* (2013.01); *A61B 17/1725* (2013.01); *A61B 17/72* (2013.01)

(58) Field of Classification Search
CPC ..................... A61B 17/1703; A61B 17/1707
See application file for complete search history.

(56) References Cited

U.S. PATENT DOCUMENTS

| 4,541,424 A | 9/1985 | Grosse et al. |
| 4,667,664 A | 5/1987 | Taylor et al. |

(Continued)

FOREIGN PATENT DOCUMENTS

| DE | 20211806 U1 | 10/2002 |
| EP | 1099413 | 5/2001 |

(Continued)

OTHER PUBLICATIONS

Gamma3™, Distal Targeting Device R2.0, Operative Technique, Stryker Osteosynthesis, Germany, 2006, 32 pgs.

(Continued)

*Primary Examiner* — Christian Sevilla
(74) *Attorney, Agent, or Firm* — Lerner, David, Littenberg, Krumholz & Mentlik, LLP

(57) ABSTRACT

A targeting device for targeting a cross bore in a bone nail has an arm member coupled to an end portion of the bone nail and an aiming portion forming part of the arm member extending parallel to a longitudinal axis of the bone nail. An adjustable aiming device is mounted on the aiming portion, the adjustable device having a guide bore alignable with the cross bore in the nail. The adjustable device is moveable with respect to the aiming portion in a direction perpendicular to a plane containing both the nail longitudinal axis and central axis of the cross bore. A target indicator is mounted on the adjustable aiming device. The target indicator has a radiolucent body including first and second spaced parallel planar portions each having a spaced radiopaque element therein.

17 Claims, 33 Drawing Sheets

(56) References Cited

U.S. PATENT DOCUMENTS

| | | | |
|---|---|---|---|
| 4,865,025 A | 9/1989 | Buzzi et al. | |
| 4,881,535 A | 11/1989 | Sohngen | |
| 4,917,111 A | 4/1990 | Pennig et al. | |
| 4,969,889 A | 11/1990 | Greig | |
| 5,031,203 A * | 7/1991 | Trecha | A61B 17/1703 |
| | | | 128/898 |
| 5,122,146 A | 6/1992 | Chapman et al. | |
| 5,433,720 A | 7/1995 | Faccioli et al. | |
| 5,478,343 A | 12/1995 | Ritter et al. | |
| 5,630,805 A | 5/1997 | Ternamian et al. | |
| 5,713,902 A | 2/1998 | Friedl | |
| 6,036,696 A | 3/2000 | Lambrecht et al. | |
| 6,039,742 A | 3/2000 | Krettek et al. | |
| 6,214,013 B1 | 4/2001 | Lambrecht et al. | |
| 6,231,576 B1 | 5/2001 | Frigg et al. | |
| 6,514,253 B1 | 2/2003 | Yao | |
| 6,520,969 B2 | 2/2003 | Lambrecht et al. | |
| 6,656,189 B1 | 12/2003 | Wilson et al. | |
| 6,932,818 B2 | 8/2005 | Behrens | |
| 7,077,847 B2 | 7/2006 | Pusnik et al. | |
| 7,175,631 B2 | 2/2007 | Wilson et al. | |
| 7,481,815 B2 | 1/2009 | Fernandez | |
| 8,231,629 B2 | 7/2012 | Lerner et al. | |
| 8,685,034 B2 * | 4/2014 | Giersch | A61B 17/1703 |
| | | | 606/86 R |
| 8,864,771 B2 * | 10/2014 | Buscher | A61B 17/1703 |
| | | | 606/96 |
| 2003/0212405 A1 * | 11/2003 | Choi | A61B 17/1721 |
| | | | 606/98 |
| 2004/0039393 A1 | 2/2004 | Robioneck et al. | |
| 2004/0167533 A1 | 8/2004 | Wilson et al. | |
| 2005/0177175 A1 | 8/2005 | Johnstone | |
| 2006/0030859 A1 | 2/2006 | Gotfried | |
| 2006/0064106 A1 * | 3/2006 | Fernandez | A61B 17/1703 |
| | | | 606/98 |
| 2006/0098851 A1 | 5/2006 | Shoham et al. | |
| 2008/0281330 A1 | 11/2008 | Ferrante et al. | |

FOREIGN PATENT DOCUMENTS

| | | |
|---|---|---|
| EP | 1356777 | 10/2003 |
| WO | 03/065907 | 8/2003 |

OTHER PUBLICATIONS

Gamma3™, Long Nail R2.0, Operative Technique, Stryker Osteosynthesis, Germany, 2006, 52 pgs.

H. P. Granhed, A new technique for distal screw insertion for locked nailing, Acta Orthop Scand, vol. 69 (3), 1998, pp. 320-321.

Japanese Publication, 2000 (one shot guide).

One Shot Device, Gamma Locking Nail Instruments, Operative Technique, Stryker Trauma, 2000.

Operative Technique, One shot Device, pp. 25 and 34, date not known.

* cited by examiner

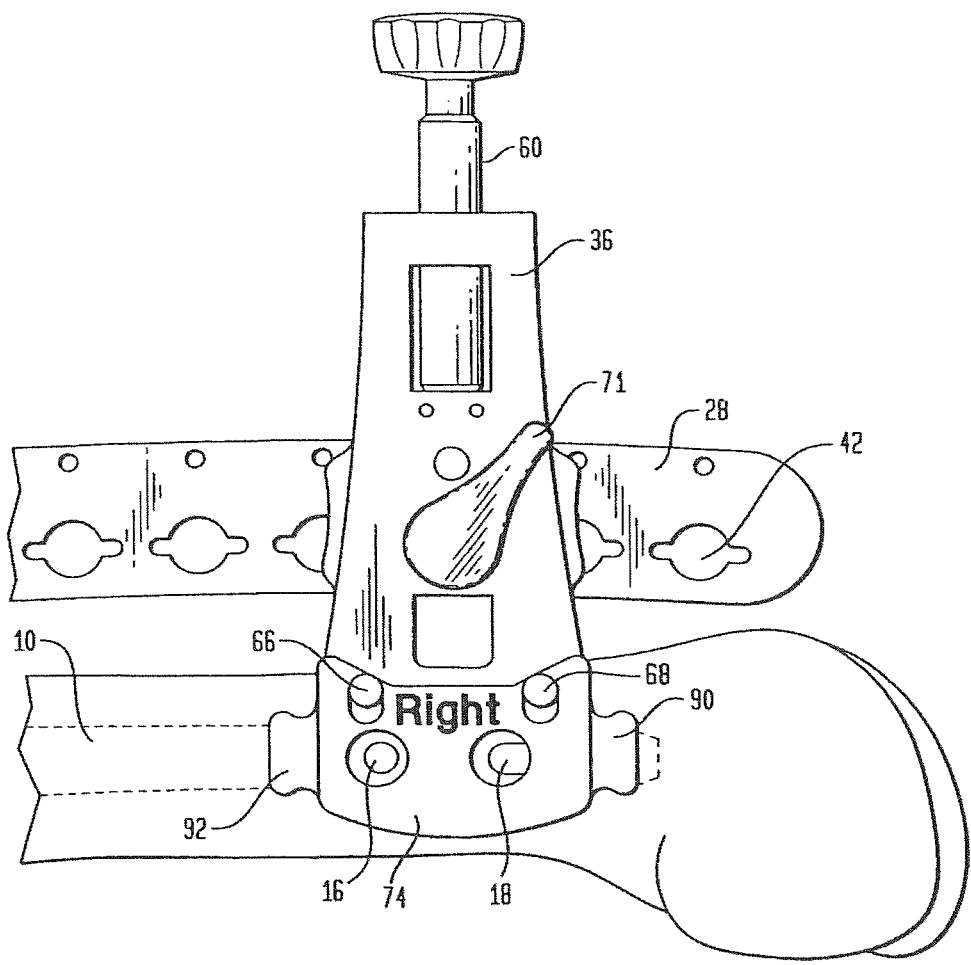

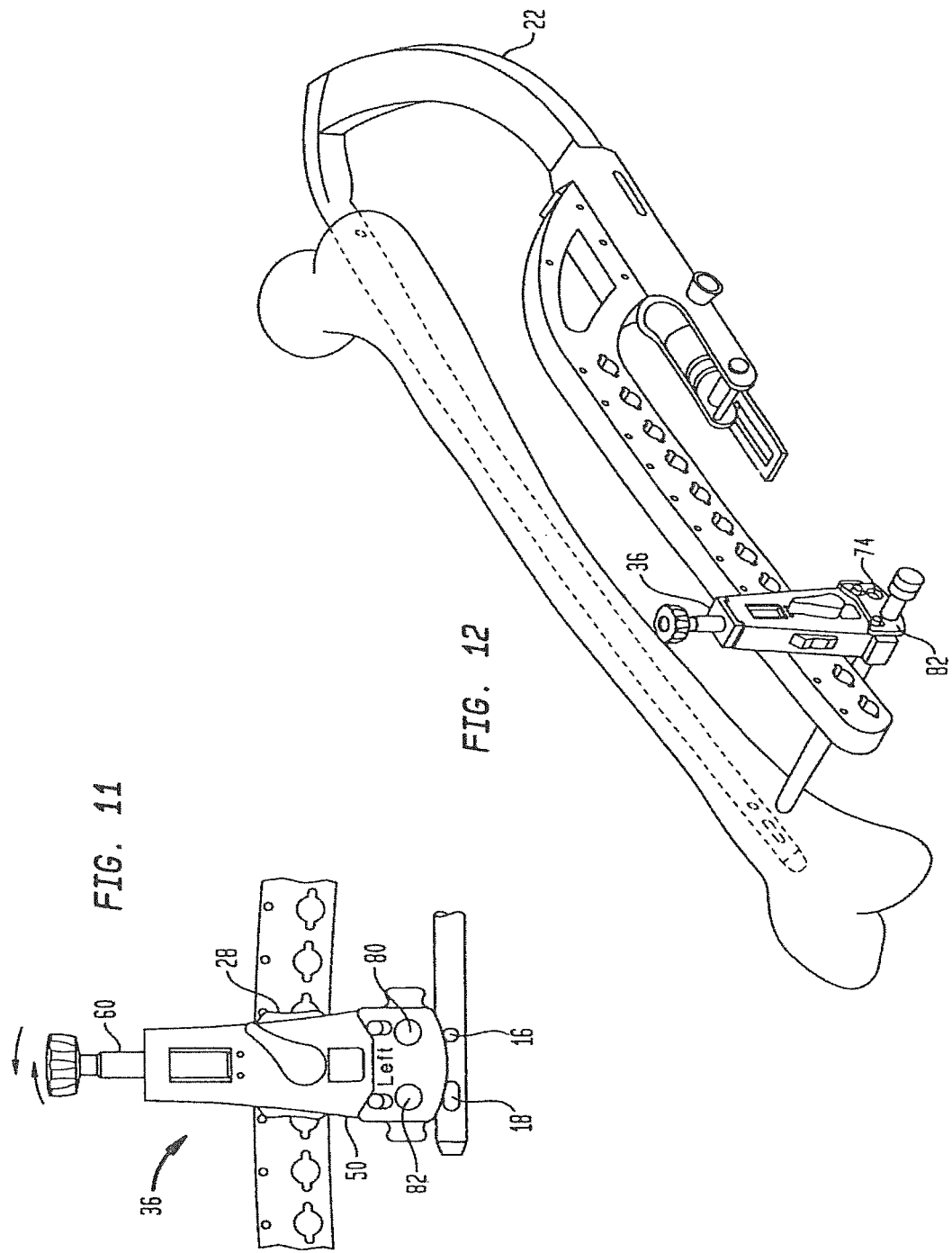

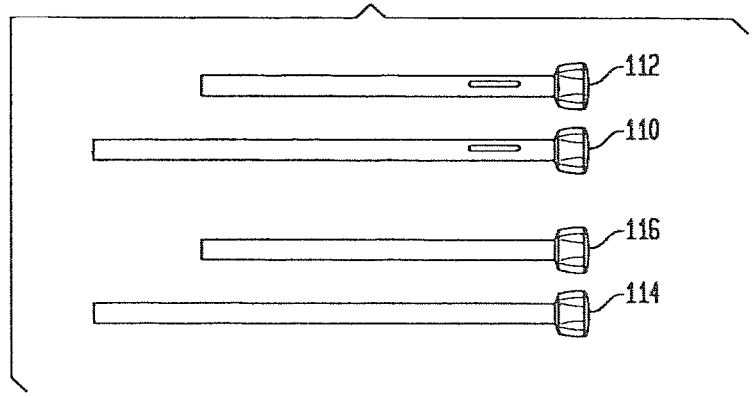
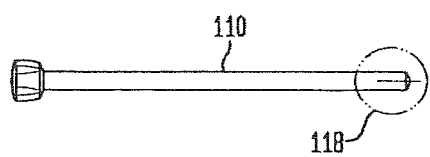
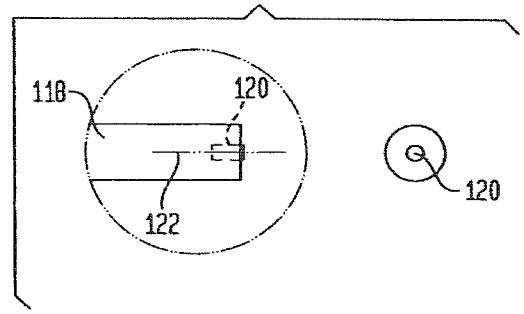
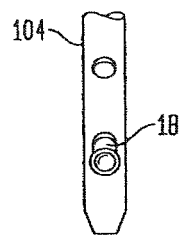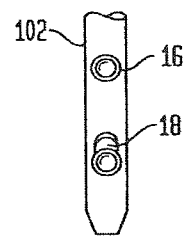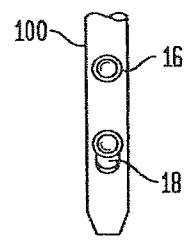

FIG. 16A
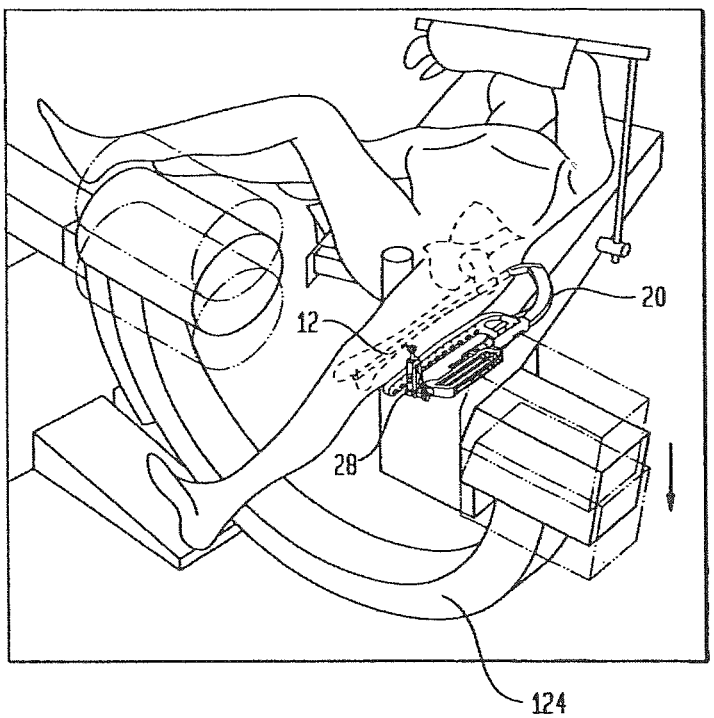
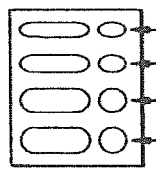 — Not in line with the nail holes
— This is the best position to drill FIG. 16B
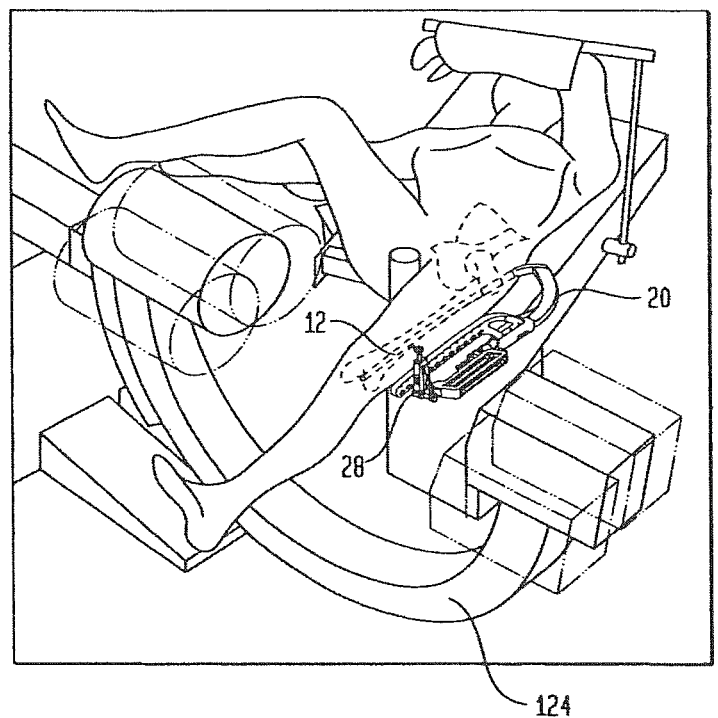
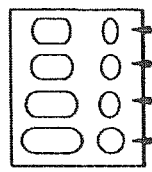 — Not in line with the nail holes
— This is the best position to drill; it shows correct view to be in line with the Nail holes

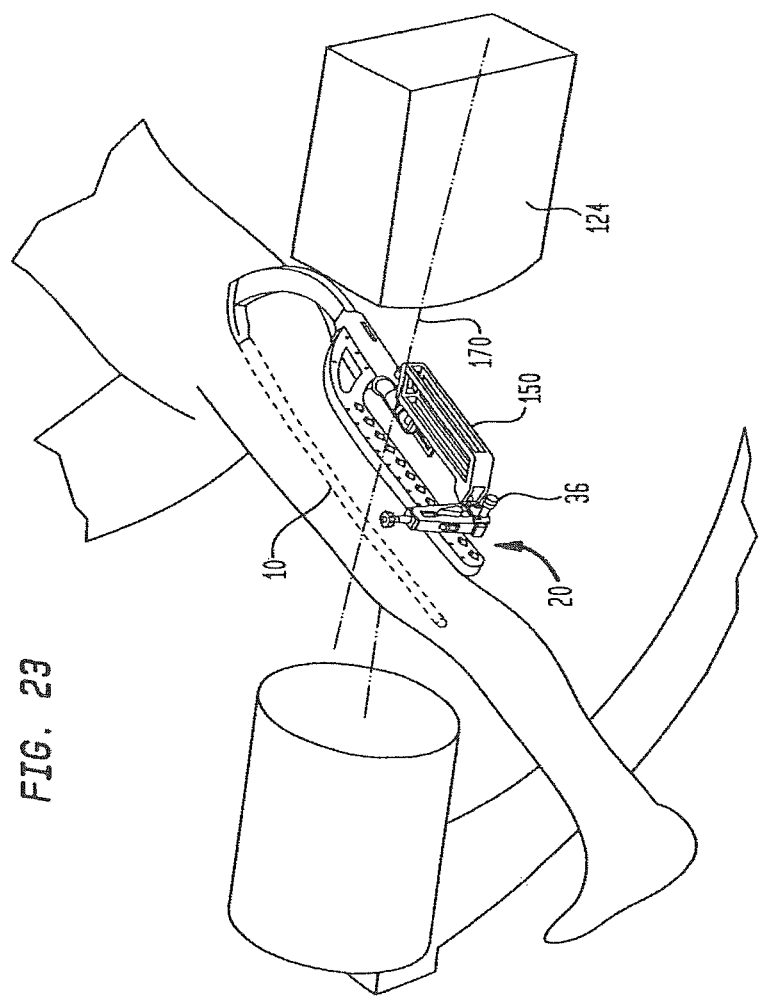

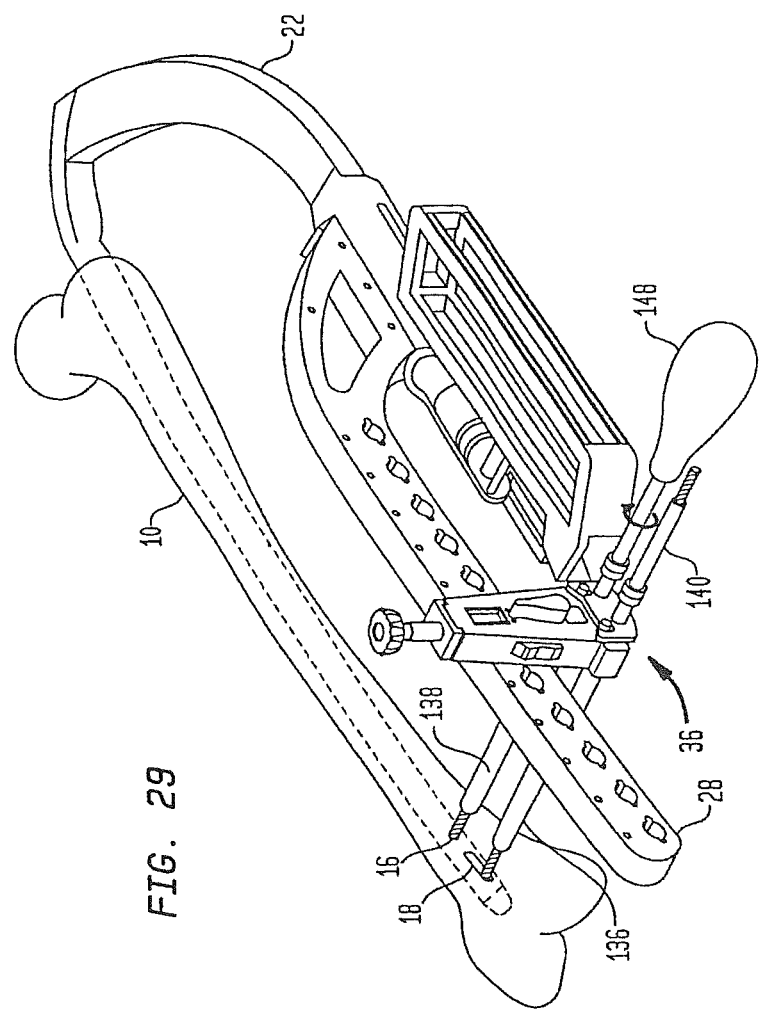

DISTAL TARGETING DEVICE

CROSS-REFERENCE TO RELATED APPLICATIONS

This application is a divisional of U.S. application Ser. No. 11/891,287 filed Aug. 9, 2007, which is a continuation-in-part of U.S. application Ser. No. 11/593,996, filed on Nov. 7, 2006, and claims the benefit of provisional Application No. 60/836,793 filed Aug. 10, 2006, the disclosures of which are incorporated herein by reference.

BACKGROUND OF THE INVENTION

In order to accurately lock long intramedullary nails (i.e. those with distal attachment screws) the distal screws have to be accurately aligned with the cross bores in the nail. This locking is complicated by the deflection of the nail during insertion into the bone canal which changes the location of the cross bore from their static position. Typically the surgeon has been forced to do this freehand with the help of an x-ray C-arm. A common problem in such a procedure is that the instruments are "in the way" since they are on the image plane of the C-arm. Furthermore, distal locking is problematic since the distal bores cannot be made precisely through the soft tissue due to the anatomical shape of the femur and the resulting curvature of the nail (here in a Z direction) which is in a plane perpendicular to a plane parallel to the frontal plane.

Intramedullary nails often provide two distal openings or cross bores for distal locking. For distal locking a nail may offer three locking options to be used, depending on the fracture pattern. To accomplish this a proximal round hole is provided and a more distal oblong hole. Distal locking is recommended if the fracture is unstable, if rotational stability is required or if there is a wide disparity between the diameter of the nail and the femoral cavity.

The first possibility is placing a locking screw in the distal part of the oblong hole. This creates a dynamic locking mechanism i.e. allows the nail to move distally and requires only one screw. Alternatively, one screw may be placed in the distal part of the oblong hole and the other in the round hole. This causes a static locking of the nail and prevents movement of the nail. However, if dynamization is required after a period of time, the screw, placed in the round hole, may be removed leaving only the screw at the distal end of the oblong bore. This method requires two screws. Lastly, one screw may be placed in the round hold and the other placed in the proximal part of the oblong hole. Again this produces static locking and requires the placement of two screws.

Various techniques can be used to guide drilling and insertion of screws through the distal holes. The freehand technique described above as well as targeting instruments such as used in a straight on approach of the imaging device described below.

The essential initial step in distal targeting is to position the fluoroscope so that the circular distal hole in the nail appears perfectly round. Naturally, this visualization cannot be used with the oblong hole. If the round hole appears to be elliptical in either the vertical or horizontal plane, the fluoroscope image position must be adjusted appropriately. It is advised to correct the image in one plane at a time.

Once an image intensifier is correctly positioned a tip of a drill is placed at the center of the hole and a hole drilled through the first cortex which in a femur is the lateral cortex and the nail cross bore until resistance of the second cortex is felt. The drill typically has a scale for measuring the required screw length.

Alternatively, a hole can be drilled through the second cortex while viewing the image. The required screw length can then be read directly from the screw scale on the drill. If a tissue protection sleeve is used around the drill, it has to be removed for the measurement. It is also possible to measure the correct screw length using a free hand screw gauge which can engage the medial cortex outer surface when the nail is in the femur. This is done after drilling through the second cortex by removing the drill and advancing the small hook of the screw gauge through the holes behind the medial cortex and read out the required locking screw length.

Typically the distal locking screw, which is usually a 5 mm screw, is inserted through the skin by using a screwdriver. The screw head is advanced carefully until it is just in direct contact with the cortex. Any targeting instrumentation used is then removed.

SUMMARY OF THE INVENTION

The present invention is intended to make locating the screws easier and more accurate. An aiming or targeting arm is attached to a known nail-holding arm. In a preferred embodiment a fixation bolt is used to hold a targeting apparatus including the aiming arm in a bore of the nail-holding arm. A clamping device with a hand locking mechanism may also be used to hold the targeting apparatus in the nail holding arm. A radiolucent adjusting device (adjustable in the Z direction) is slid on to the aiming arm by means of a pin inserted in a corresponding opening in the aiming or targeting arm and secured by turning a lever. On the aiming arm there are a series of holes with each hole having a number that corresponds to the respective nail lengths (and thus to the corresponding location of the distal bores in each nail).

A radiolucent target indicator, which is slipped onto a dovetail guide found on the adjusting device, is the system with which the exact position located on the level of the holes in the nail is found. This is preferably done by using an oblique x-ray. This positioning is achieved by aligning two planes, lying one behind the other on the target indicator, in parallel with respect to the longitudinal axis of the nail. For this the ribs of the target indicator, which are otherwise transparent to x-rays, have x-ray markings. In the first plane, there are bead-like x-ray strips, such as dashed wires. In the second plane uniform straight (solid) wires are used so that in correct Z positioning, on the x-ray image, only two pairs of lines at a distance from each other (dashed-straight) are recognizable. The wires and strips are not aligned in the Z direction (i.e. the solid wires are preferably spaced apart further than the dashed wire so that each wires lies in a different plane in the Z direction.

The x-ray images may appear, for example, as follows:

First the x-ray C-arm is aligned. The image is as below if the angle alignment is incorrect.

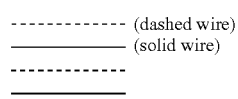

Here x-ray C-arm is in correct alignment (median-lateral and x/y-plane).

Lastly, the adjusting device is adjusted so the hole position of the nail in the Z plane In a correct Z position, the position of the bore is outside the solid indicators and the Z position can then be readjusted with the help of the adjusting screw of the adjusting device until the solid wires straddle to the central axis of the distal bores in the nail.

X-ray markers in radiolucent locating arms for target devices are known from U.S. Pat. No. 6,036,696 as well as the brochure entitled *Gamma Long Nail R* 2.0 Operative Technique P. including illustrations. This oblique x-ray operative technique is also known in its fundamental characteristics from an article by Hans Granhead, *A New Technique Of Distal Screw Insertion For Locked Nailing*, Acta Orthop Scan 1998 69(3): 320-321.

Advantageously, by means of the oblique C-arm method, a freer access for the distal through-boring of the femur is achieved and so the dangers of drilling under x-ray imaging are minimized. The targeting apparatus of the present invention provides a novel method of locating the cross bores in a bone nail.

In order to deliver reproducible results with the targeting apparatus of the present invention the adjusting device can be adjusted in the Z direction with an adjusting screw thread having no play. This may be accomplished by using a cover mounted on the main body of the adjusting device, an O-ring, the thickness of which is slightly greater than the recess provided for it in the body of the adjusting device. The cover is pressed on and the adjusting screw is screwed into the threads in the body, so that the elastic O-ring stretches the sides of the adjusting screw against the sides of the thread and takes the play out of the connection.

A plastic template or a guide plate is used by the operator in the readjustment of the desired positioning in view of the type of locking, i.e. static or dynamic position. For this the corresponding template or guide plate (right or left nail) is placed on the adjusting device preferably using a click-mechanism.

The instruments of the present invention are designed to facilitate minimally invasive surgery and reduce the operating room (OR) time down to a minimum by the aid of using new instrumentation and an optimized surgical technique.

The nails have a proximal diameter of 15.5 mm to help minimize the incision length required for minimally invasive surgery. Nevertheless, they offer the same biomechanical strength and cut-out resistance. A major advantage of the instrument platform of the present invention is that the instruments are designed for a minimally invasive surgical technique and reduce OR time to a minimum. The instruments are easy to use and easy to clean and can be used with a variety of intramedullary nails.

The targeting device of the present invention offers the competitive advantages of minimizing fluoroscopy time, helping to avoid misdrilling and easy calibration for each type of Gamma3 long nail. The targeting device is mainly made out of radiolucent carbon fiber material to overcome the problem of x-ray artifacts. This will help the surgeon in getting an optimal accurate surgical result.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

The invention relates to a targeting device for targeting a cross bore in a bone nail which includes an arm member coupled to an end portion of a bone nail and an aiming portion forming part of the arm member extending parallel to a longitudinal axis of the bone nail. An adjustable aiming device mounted on the aiming portion, the adjustable device having a guide bore alignable with the cross bore in the nail. The adjustable device is moveable with respect to the aiming portion in a direction perpendicular to a plane containing both the nail longitudinal axis and central axis of the cross bore. A target indicator mounted on the adjustable aiming device. The target indicator has a radiolucent body including first and second spaced parallel planar portions each having a spaced radiopaque element therein. The adjustable aiming device is moveable in a longitudinal direction along the portion of the arm member extending parallel to the bone nail. Preferably, the target indicator includes a pair of spaced radiopaque elements in both the first and second planar portions. The radiopaque elements in the first planar portion are preferably spaced closer to each other than the radiopaque elements in the second planar portion. In the preferred embodiment the first and second planar portions extend perpendicular to a plane containing the central axis of the nail cross bore and containing a longitudinal axis of the nail adjacent the cross bore. The adjustable aiming device is made of a radiolucent material. The guide bore on the aiming device is formed in part by a radiopaque template having a bore therein aligned with the nail cross bore, the template removably mounted on the adjustable aiming device adjacent the guide bore. The nail includes two cross bores spaced along the longitudinal axis of the nail and the adjustable aiming device and template have two bores alignable with the two nail cross bores. One of the cross bores in the nail is elongated in the direction of the longitudinal axis of the nail. In the preferred embodiment the aiming portion of the arm member includes a series of bores along the length thereof for receiving a support pin extending from the adjustable aiming device. The arm member preferably has a connector element at an end thereof opposite an end coupled to the bone nail, the connector for releasably engaging the aiming portion. A method is provided for locating a cross bore in an intramedullary nail which includes inserting an intramedullary nail having a cross bore in a bone canal, coupling a targeting arm to the intramedullary nail, the targeting arm having a portion extending parallel to a longitudinal axis of the nail, mounting an adjusting device having a cross bore drill guide to a central axis of the bore and the nail longitudinal axis, the adjusting device drill guide moveable in a direction perpendicular on the portion of the targeting arm extending parallel to the nail longitudinal axis, the adjusting device having a target indicator coupled thereto having two sets of parallel radiopaque elements thereon, aligning the two sets of parallel radiopaque elements in an x-ray beam, and locating the cross bore in the nail by centering the cross bore in the x-ray beam between the two sets of parallel radiopaque elements if necessary by moving the adjusting device. A distance between the first set of parallel radiopaque elements is less than the distance between the second set. Preferably the first set of radiopaque elements are solid pins and the second set of radiopaque elements are a series of connected bead elements. The locating of the plane parallel to the frontal plane is accomplished by placing the solid pins within the series of connected bead elements at the same spacing as on the target indicator. The first set of radiopaque elements are solid pins and the second set of radiopaque elements are a series of connected bead elements.

Preferably a plane containing ends of the radiopaque elements of the first and second sets of radiopaque elements forms a non zero angle with a plane containing the first set of parallel radiopaque elements and a plane containing the second set of parallel radiopaque elements. A fracture fixation system is also provided for a long bone comprising: a bone nail having at least one cross bore and preferably a pair of cross bores therethrough. An arm member is coupled to an end portion of the bone nail, wherein the arm member comprises an aiming portion extending parallel to a longitudinal axis of the bone nail. An adjustable aiming device is mounted on the aiming portion. The adjustable aiming device has a guide bore alignable with the cross bore in the nail. The adjustable aiming device is moveable with respect to the aiming portion in a direction perpendicular to a plane containing both the nail longitudinal axis and central axis of the cross bore. A target indicator is mounted on the adjustable aiming device, the target indicator having a radiolucent body including first and second spaced parallel planar portions each having a spaced radiopaque element therein.

BRIEF DESCRIPTION OF THE DRAWINGS

FIG. 10 is an identical view to FIG. 9a with the adjusting device in a locked position;

FIG. 11 is a partial elevation view showing the adjusting device prior to the holes in the guide template being aligned with the cross bores in the bone nail in the Z direction;

FIG. 12 shows an isometric view of the entire targeting apparatus including adjusting device with a radiolucent tissue protection sleeve mounted therein;

FIG. 13 shows a pair of radiolucent trocars both long and short and a pair of radiolucent tissue protection sleeves to receive the long and short radiolucent trocars;

FIGS. 14 and 14A are elevation views of a radiolucent trocar equipped with a radiopaque element in the tip of the trocar;

FIGS. 15A, 15B and 15C are views of the distal ends of three bone nails, each having a pair of cross bores showing the location of a bone screw when dynamic locking, secondary dynamization locking or static locking is desired;

FIG. 16A and FIG. 16B show the targeting apparatus of the present invention mounted on a bone nail inserted into the femur of a patient located in a c arm X-ray machine which can be adjusted both in an x-y plane parallel to a frontal plane of the body and in a Z direction lying in a plane parallel to the sagittal plane of the body;

FIG. 18 is a partial isometric view of the targeting apparatus of the present invention including the adjusting device with a drill guide and dull bit mounted therein for drilling a hole in the bone surrounding the nail for insertion of a bone screw;

FIG. 23 is an isometric view showing the targeting apparatus of the present invention including target indicator mounted on the adjusting device with an X-ray beam extending at an oblique angle therewith;

FIG. 28 is an isometric view of the target apparatus assembly including adjusting device and target indicator with a tissue protection sleeve mounted thereon to guide a trocar and forming an incision prior to drilling the bone for receipt of a bone screw;

FIG. 29 is a view similar to FIG. 20 showing the insertion of the second bone screw in a cross bore of a bone nail after the bone has been dulled when using the oblique approach;

DETAILED DESCRIPTION

Figure 1:
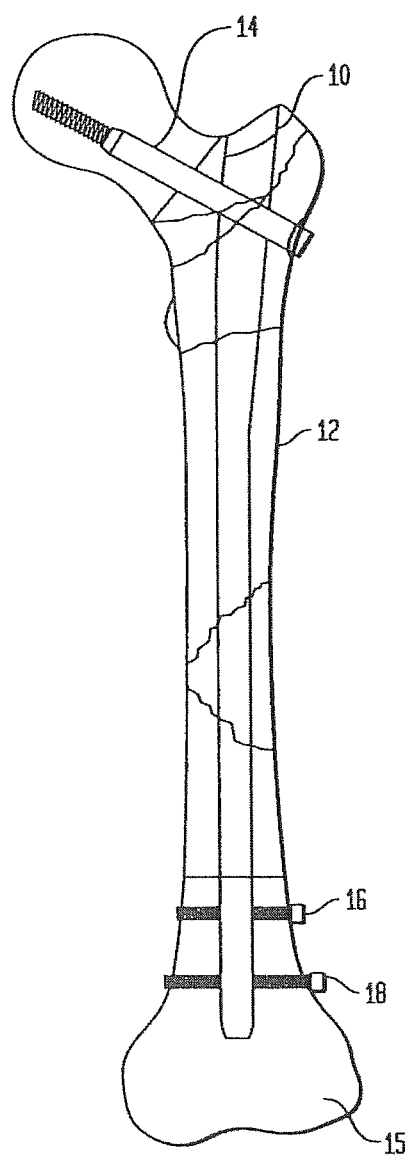
FIG. 1 is an elevation view of a typical intramedullary fracture fixation nail for the femur having a pair of distal bone screws extending through the cortex of a long bone.

Referring to FIG. 1, there is shown a typical intramedullary nail 10 used for fracture fixation such as sold by Stryker Trauma GmbH as a GAMMA® long bone nail. Nail 10, when used in a femur 12 includes a lag screw 14 for insertion into the head of a femur and a pair of distal locking screws 17 going through bore 16 and oblong hole 18, which engage the cortical bone on both the lateral and medial sides of the distal femur 15.

Figure 2:
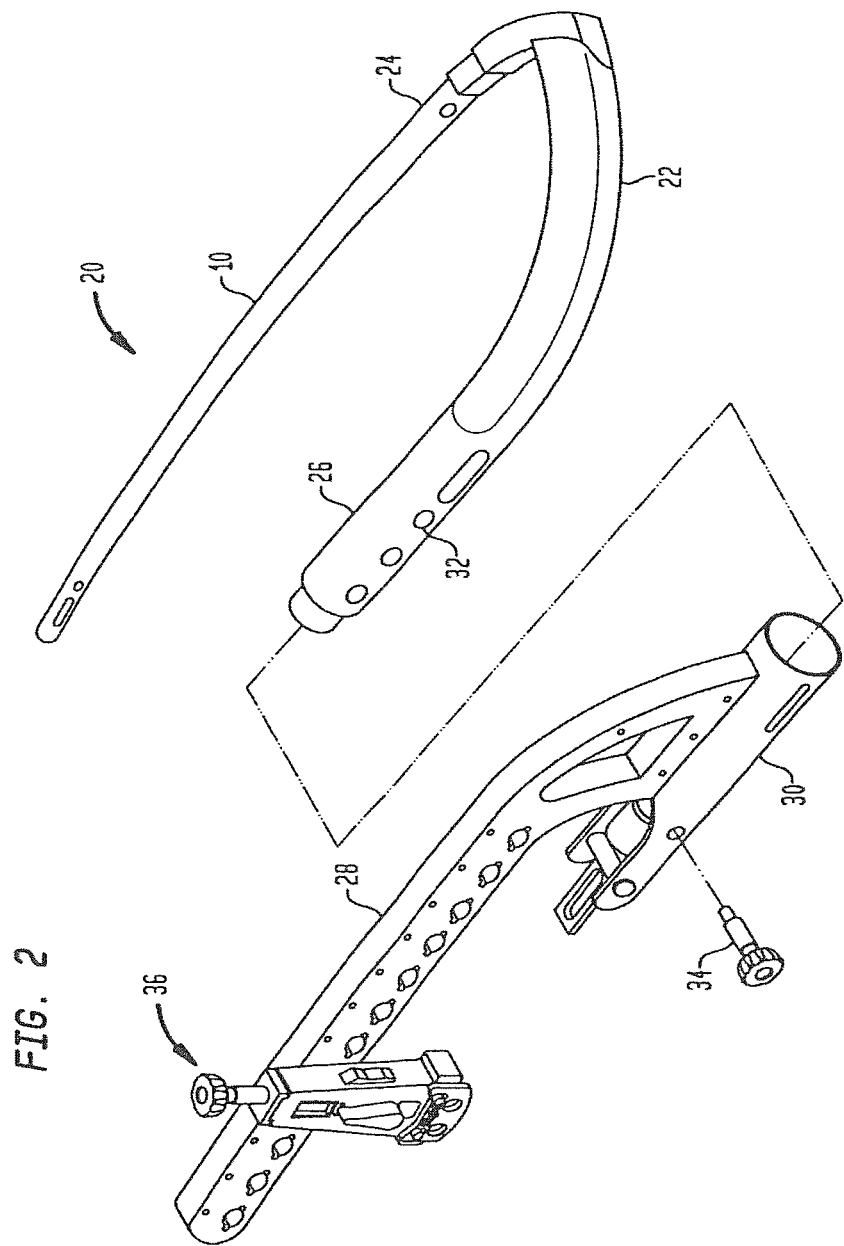
FIG. 2 is an exploited isometric view of the targeting apparatus of the present invention.

Referring to FIG. 2, there is shown a partially assembled targeting apparatus of the present invention generally denoted as 20, which includes a handle portion 22 coupled to proximal end 24 of femoral intramedullary nail 10. Handle 22 may be coupled by a threaded connection to proximal end 24 of nail 10 or in any other manner all of which are well-known in the art. In a preferred embodiment, handle 22 includes a coupling portion 26, which is adapted to receive various targeting apparatus for locating and drilling the bone for receipt of the femoral lag screw 14 and the distal bone screws bores 16 and 18. For example, such a targeting arm for a lag screw may be similar to that shown in U.S. Pat. Nos. 6,039,739 and 7,077,847, the disclosures of which is incorporated herein by reference. As shown in FIG. 2, the targeting apparatus 20 includes a distal targeting arm 28, which includes a mounting system 30 adapted to be coupled to portion 26 of arm 22. Arm 26 is provided with a series of through bores 32 for receiving a fixation bolt 34. As will be discussed in more detail below, distal targeting arm 28 includes an adjusting device 36 mounted thereon.

Figure 3:
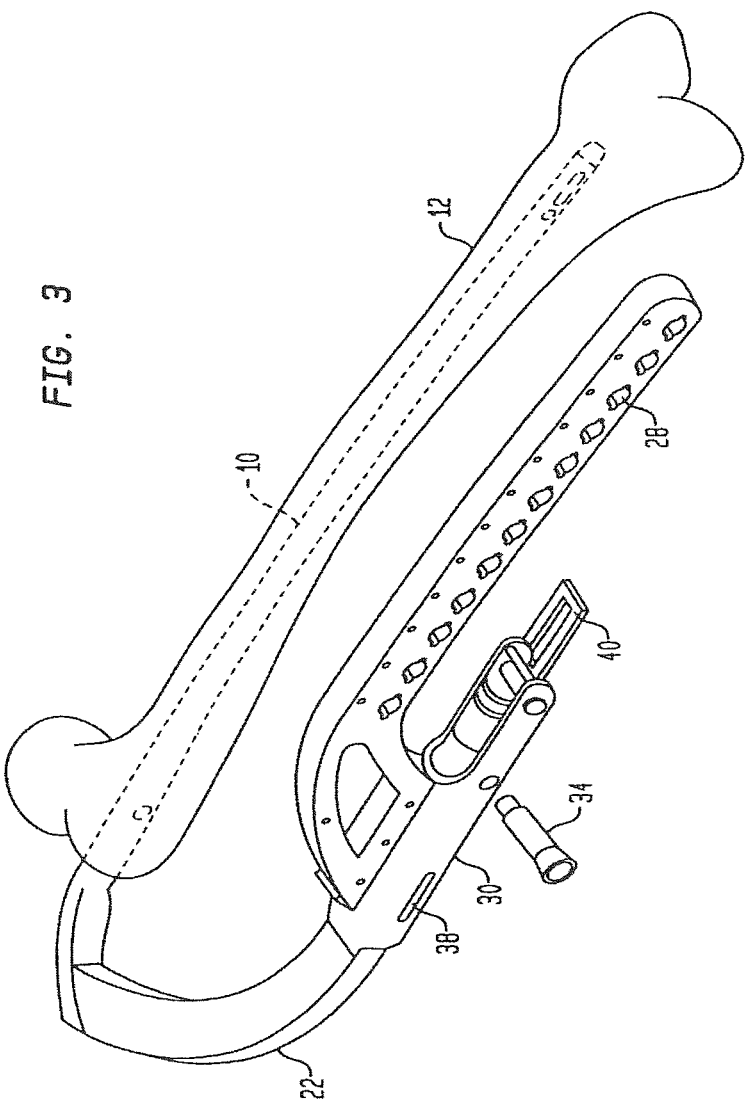
FIG. 3 is the targeting apparatus of FIG. 2 in the assembled unlocked condition with the nail FIG. 1 inserted into a femur.
Figure 4:
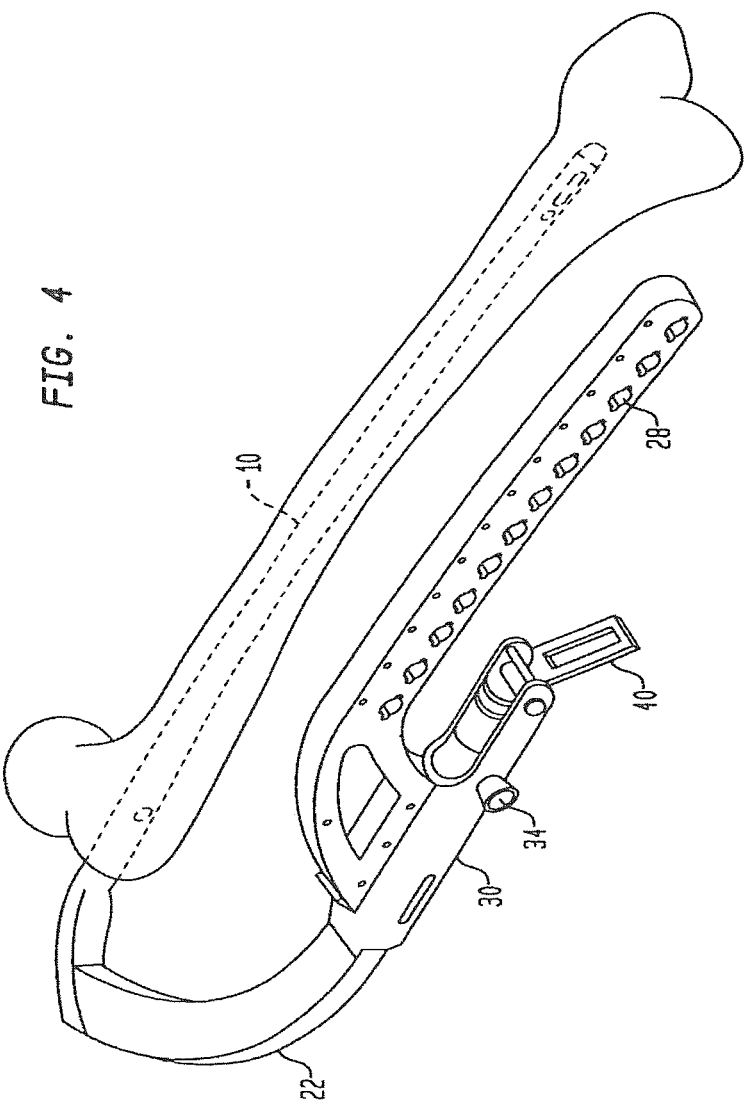
FIG. 4 is an isometric view of the targeting apparatus of FIG. 3 in a locked condition.

Referring to FIG. 3, there is shown bone nail 18 inserted into a right femur 12 with coupling apparatus 30 inserted on to portion 26 of arm 22 just prior to inserting fixation bolt 34 through one of the bores 32 in portion 26. To ensure the correct rotational alignment between coupling portion 30 and portion 26 of arm 22, a window 38 may be provided in coupling portion 30 to locate an alignment indicator formed on portion 26 (not shown). A distal targeting arm lever 40 may be provided, which is coupled to a locking member which fits within an internal bore of portion 26 such that when lever 40 is rotated, a tight frictional lock is developed between handle portion 26 and coupling portion 30. This lock position is shown in FIG. 4. Obviously any method of coupling targeting arm 28 to handle 22 may be used. It would even be possible to make the entire targeting apparatus in one piece. After the distal targeting arm is mounted to handle 22, it is located outside the body in generally parallel alignment to the longitudinal axis of nail 18.

Figure 5:
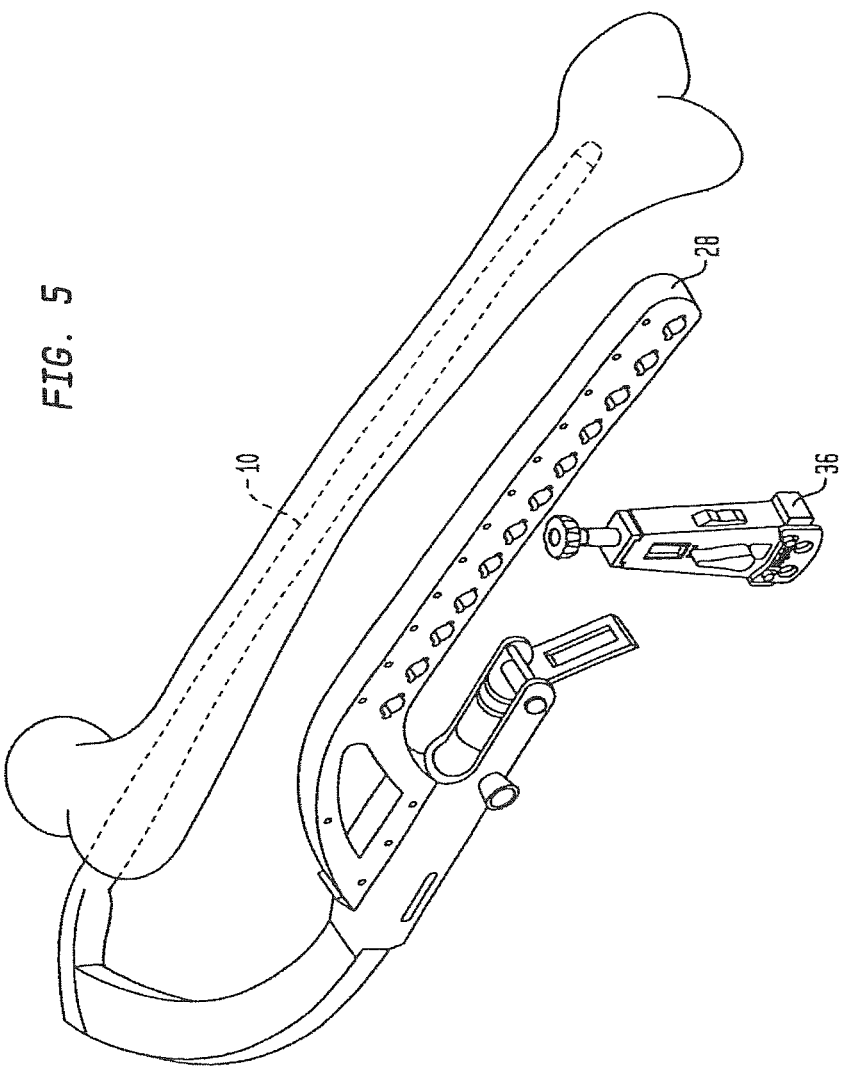
FIG. 5 is the targeting apparatus of FIG. 4 just prior to receiving an adjusting device being mounted thereon.
Figure 6:
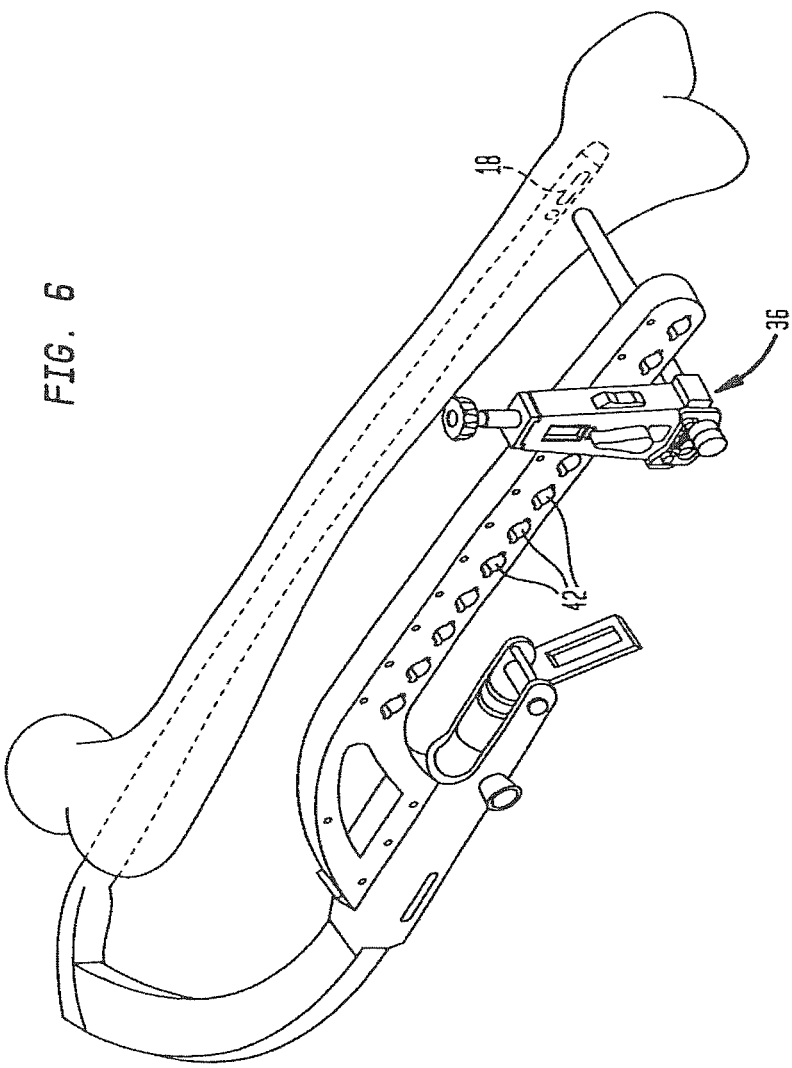
FIG. 6 is the targeting apparatus of FIG. 5 with the adjusting device mounted thereon including a radiolucent tissue protection sleeve in the adjusting device.

Referring to FIGS. 5 and 6, there is shown adjusting device 36 immediately prior to its mounting on distal targeting arm 28. Adjusting device 36 is mounted in one of a series of bores 42 on distal targeting arm 28. Each of the bores 42 locates the adjusting device 36 in correct alignment for one of a series of different length bone nails. Obviously the shorter the nail, a bore 42 closer to the proximal end of nail 18 is used. When mounted in the proper hole 42 for a given length nail, the adjusting device is in alignment with the cross bores 16 and 18 at the distal end of the nail 10. It should be noted that both arm 28 and adjusting device 36 are made of a radiolucent material such as PEEK (polyetheretherketone).

Figure 7:
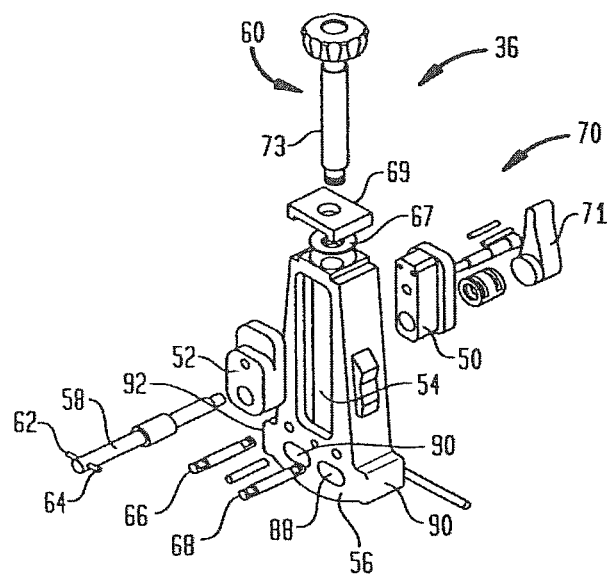
FIG. 7 is an exploited view of the adjusting device shown in FIGS. 5 and 6.

Referring to FIG. 7 there is shown an exploded view of the adjusting device 36. Device 36 includes a pair of adjustable members 50 and 52 which can be moved up and down within a cavity 54 in a body 56 of device 36. A coupling pin 58 extends through members 50 and 52 and therefore moves vertically within cavity 54 upon actuation of an adjusting screw 60. Pin 58 includes a pair of radially extending tabs 62 and 64, which are received within slotted recesses 43, 45 which open into bores 42 of arm 28. (See FIG. 9A.) Tabs 62 and 64 prevent rotation of pin 58 after insertion into bore 42. Also mounted in body 56 are a pair of support pins 66 and 68, which are used to mount a template shown in FIG. 8. A locking mechanism generally denoted as 70 is provided which is capable of locking moveable elements 50 and 52 and therefore pin 58 in a desired vertical position within cavity 54 of body 56. Thus, when assembled and when pin 58 is mounted in bores 42 of adjusting arm 28, the adjusting device body 56 may be moved up and down in the Z direction by the rotation of screw 60. In the preferred embodiment screw 60 is designed to have no play so that accurate adjustments can be made. This may be accomplished with an o-ring 67 and cover 69 which forces the o-ring against shaft 73 of screw 60. Body 56 includes a pair of dovetail shaped extensions 91, 92 on each side surface. When a desired location is reached, the locking mechanism 70 may be actuated by turning lever 71 to lock the body 56 with respect to pin 58. Obviously, there are many other ways to design the adjusting device. However, what is essential is that the adjusting device body 56 may move relative to pin 58, at least in the Z direction, after being mounted on arm 28.

Figure 8:
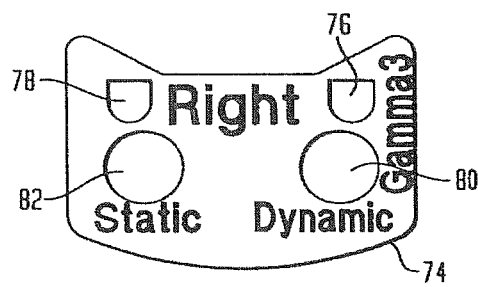
FIG. 8 is an elevation view of a tissue protection sleeve guide template for use with a right femur.

Referring to FIG. 8, there is shown a right template 74 to be used with the adjusting device 36. Template 74 includes a pair of mounting openings 76 and 78 and a pair of bores 82 for use in locating the cross bores in the bone nail, guiding a drill for drilling cortical bone adjacent the cross bores and for inserting bone screws in the cross bores. While a template 74 for a right femur is shown the template for the left femur would be similar with holes 80 and 82 ("dynamic" and "static") reversed. The "static" and "dynamic" markings refer to the location of the bone screws in circular bores 16 and oblong bore 18 as discussed below. Template 74 includes openings 76 and 78 for mounting the template on the pins 66 and of adjusting device 36. Since template 74 is made of plastic, one way to provide left and right template 74 is to mold the necessary markings for the right template on one side and the markings for the left template on the other side.

Figure 9:
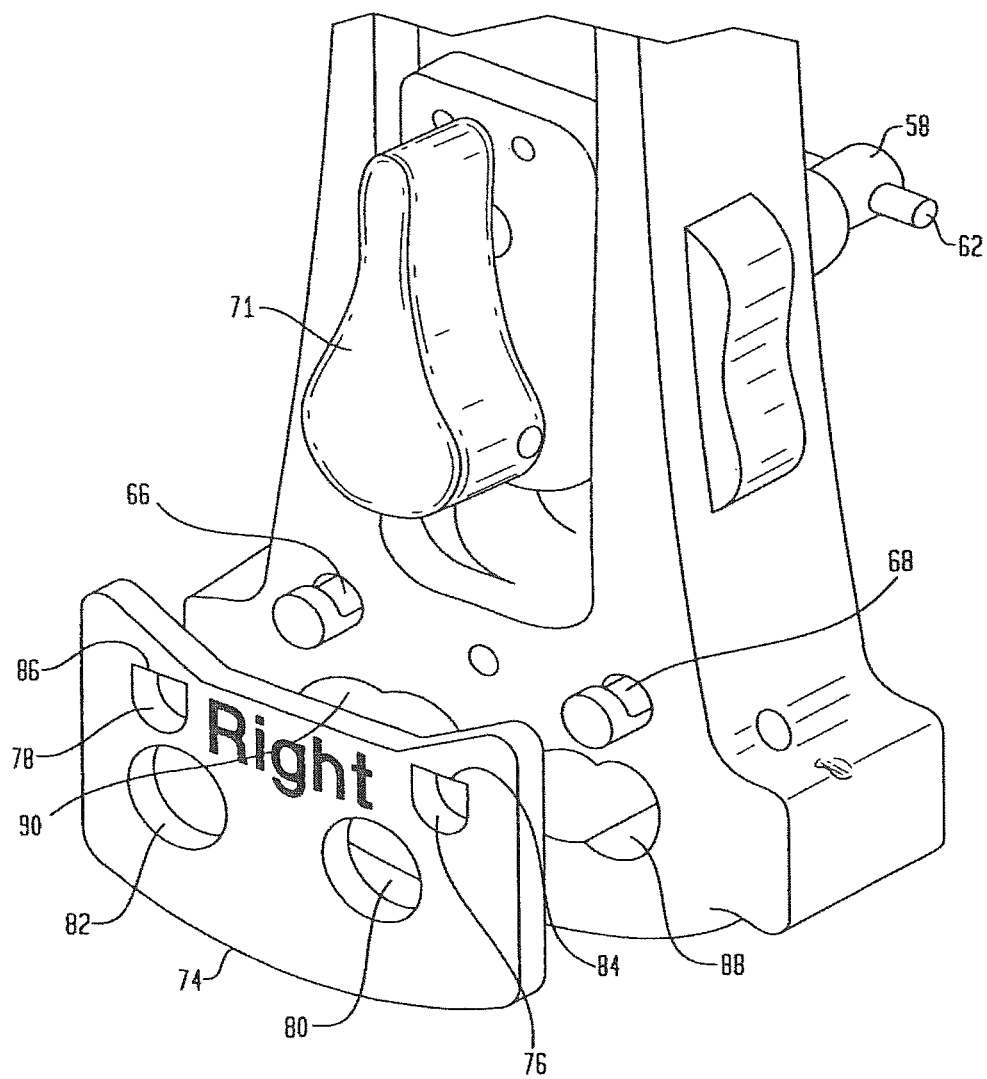
FIG. 9 is an enlarged view of a portion of the adjusting device just prior to the template of FIG. 8 being mounted thereon.

Referring to FIG. 9, there is shown right template 74 just prior to being mounted on pins 66 and 68 of the adjusting device. As can be seen in FIG. 9, pins 66 and 68 are generally cylindrical but have recess portions 69 for receiving upper flat surfaces 84 and 86 of opening 76 and 78. Thus, template 74 is located on pins 66 and 68 and then slid downwardly in FIG. 9 to lock template 74 on the adjusting device. It should be noted that adjusting device 36 has oblong bores 88 and 90 so that different spacings between bores 80 and 82 of template 74 can be accommodated. This would be required when secondary dynamization is required.

Figure 9A:
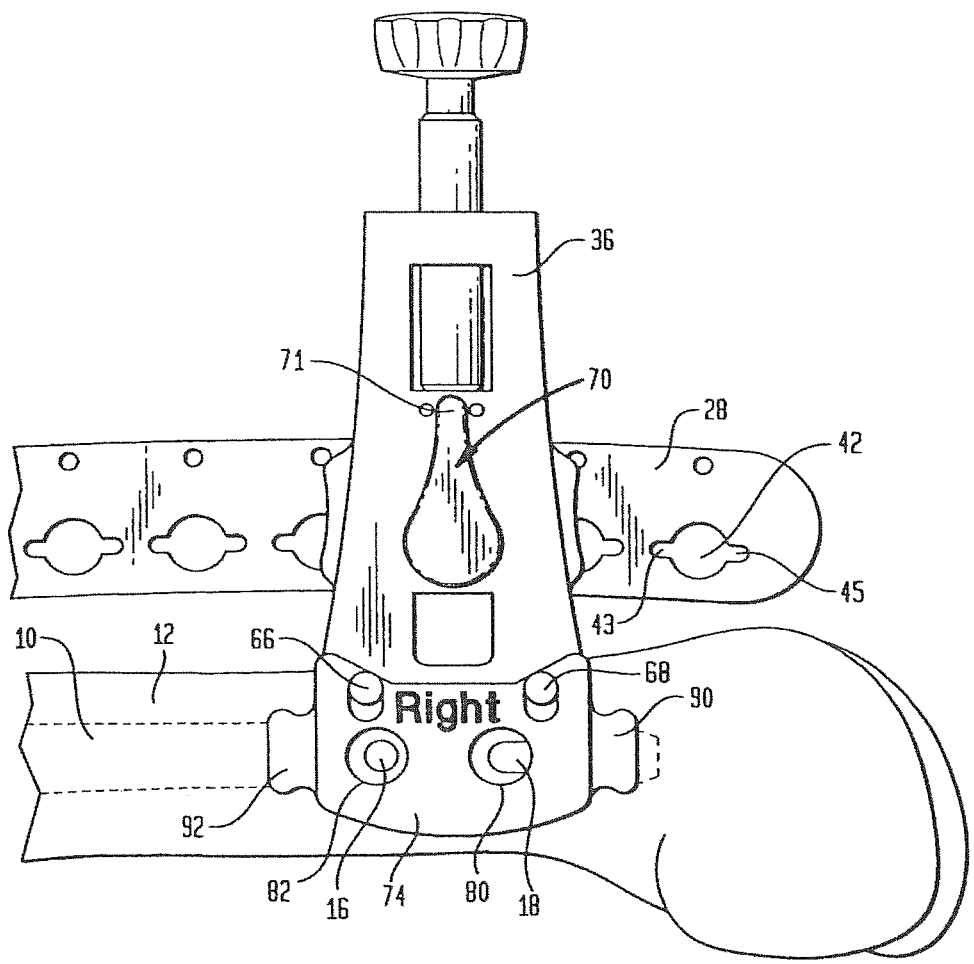
FIG. 9A is an elevation view showing the adjusting device mounted on an end of the targeting apparatus with the bores in the guide template aligned with the bores in the bone nail in with the adjusting device in an unlocked position.

FIG. 9A shows the adjusting device 36 mounted on arm 28 with the bores 80 and 82 aligned with circular bore 16 and the proximal end of oblong bore 18 of nail 10. In the position shown in FIG. 9A locking system 70 is in the unlocked position. Referring to FIG. 10, lever 71 of locking system 70 is moved to the locked position thereby fixing the adjusting device 36 and template 74 in the desired position. Also shown in FIGS. 9A and 10 are the pair of dovetail-shaped mounting elements 91 and 92 formed on the sides of body 56 of adjusting device 36. The function of these dovetail-shaped elements 91 and 92 will be discussed in more detail below.

Referring to FIG. 11, in contrast to FIGS. 9A and 10, adjusting device 36 is shown in an incorrect position in the Z direction, whereby the surgeon must adjust the template position by turning screw 60 to thereby move body 56 of adjusting device 36 until correct alignment is achieved. It should be noted that the template 74 in FIG. 11 in a left template has holes 80 and 82 located closer together than that shown in the right template 74 of FIG. 8, which allows the bone screw being inserted in oblong hole 18 to be at the proximal most portion of the oblong hole 18 whereas the template of FIG. 8 has a wider spacing so that the bone screw will be located at the distal most end of oblong hole 18. The closer hole location on template 74 will produce static locking whether the template is a right or a left template. This is best shown in FIG. 15 wherein the right most nail 100 shows the bone screws are positioned for static locking to prevent the nail from moving distally within the medullary canal. The central FIG. 102 is referred to as secondary dynamization in which the nail can move distally if the bone screw in round cross bore 16 is removed. Dynamic locking is shown in nail section 104 in which the nail may move distally about the single cross-locking screw in oblong hole 18. The spacing between the two screws is greater in nail 102 versus nail 100 so that two different left and right templates 74 are required.

Referring to FIG. 12, there is shown the targeting apparatus with adjusting device 36 mounted thereon including a radiolucent tissue protection sleeve 106 mounted within hole 82 of template 74. A tissue protection sleeve helps guide a trocar and a drill into alignment with the cross bore in the distal end of nail 10 and protects the tissue when drilling through the cortical bone of the distal femur.

Referring to FIG. 13, there is shown long and short radiolucent trocars 110 and 112, respectively, and long and short radiolucent tissue protection sleeves, 114 and 116, respectively. Tissue protection sleeves 114 and 116 are tubular with a bore there through for accommodating the radiolucent standard trocar for cutting tissue and a drill bit for drilling a hole in the cortical bone of the femur. Both long and short trocars and sleeves are provided to accommodate different size patients. However, use of the short trocar is preferred since there will be less angular error between the support on the adjusting device 36 and the end of the sleeve.

Referring to FIG. 14, there is shown long radiolucent trocar 110 which has a tip 118 including a radiopaque element 120 along its central axis 122. The short radiolucent trocar has the identical tip structure including radiopaque target member 120. The radiolucent trocars are used for targeting the cross bores in the nail as will be discussed below in connection with the straight on x-ray beam approach. As discussed above, the short sleeve is preferred. The tissue protection sleeves 114 and 116 need to be of a sufficient length to contact the cortical surface of the bone to thereby protect the tissue during the drilling operation.

Figure 17A:
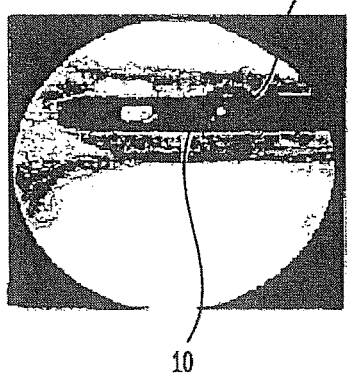
FIGS. 17A through 17C show the process of aligning the radiolucent trocar of FIG. 14 when mounted in the adjusting device to locate a cross bore in the nail when using a straight on X-ray beam approach.
Figure 17B:
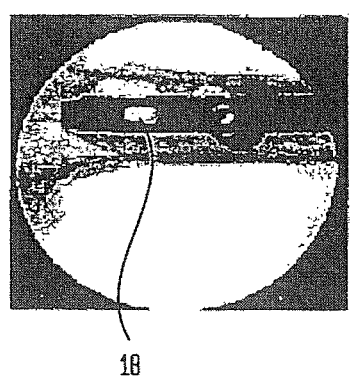
Figure 17C:
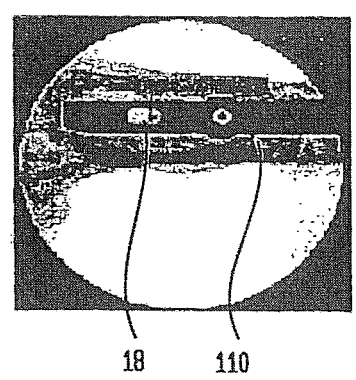
Figure 1B:
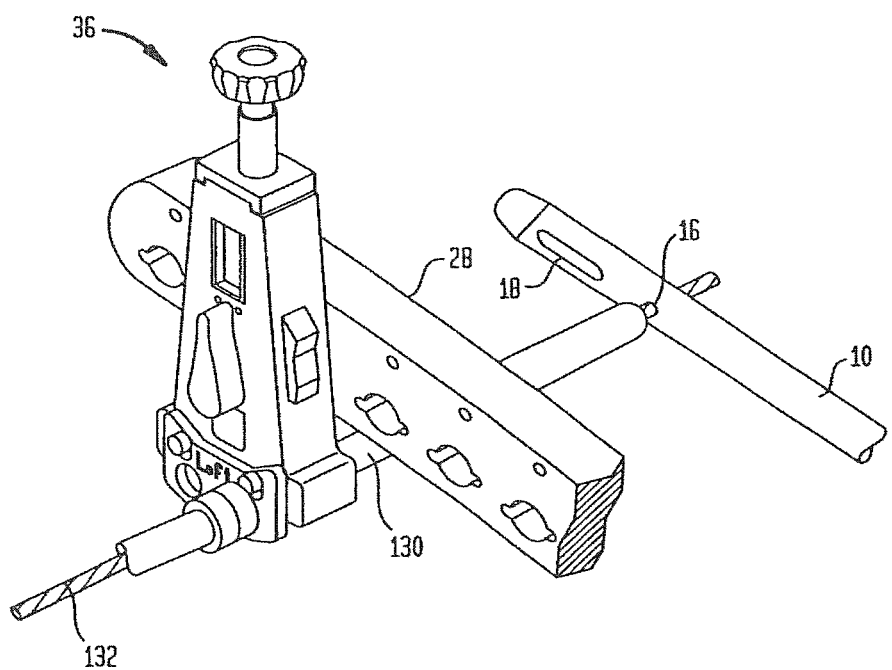

Referring to FIGS. 16A and B, there is shown the use of a standard adjustable x-ray imaging device in a straight on approach with a patient's leg inserted in the x-ray beam path. The targeting apparatus 20 of the present invention is mounted on a nail which has been inserted into the medullary canal of, in the case of FIGS. 16A and 16B, the left femur. The figures show the movement of the imaging device to align the fluroscope 124. The essential initial step in distal targeting is to position the fluoroscope image so that the distal hole 16 in the nail appears perfectly round. Naturally, this visualization step refers to the appearance of the round hole and not the oblong hole 18. If the hole appears to be elliptical in either the vertical or horizontal plane, the image intensifier position must be adjusted appropriately as shown in the schematic diagrams in FIGS. 16A and 16B. It is advised to correct image in one plane at a time. Radiolucent trocar 110, 112 is equipped with a radiopaque element in the tip of the trocar. This helps to determine the exact position of the trocar in the straight on approach. FIGS. 17A through 17B show the use of the radiolucent trocars, either 110 or 112, to locate the bore 16 in the straight on x-ray beam approach. FIGS. 17a through 17c are the fluoroscope images seen by the surgeon with the properly located radiolucent trocar shown in FIG. 17c.

Referring to FIG. 18, there is shown the targeting arm with the adjusting device 36 mounted thereon in the locked position with long sleeve 130 mounted in hole 82 of a left template to guide a drill 132 through the cortical bone on the lateral side of the femur, through the cross bore 16 of nail 10 and through the cortical bone on the medial side of the femur.

Figure 19:
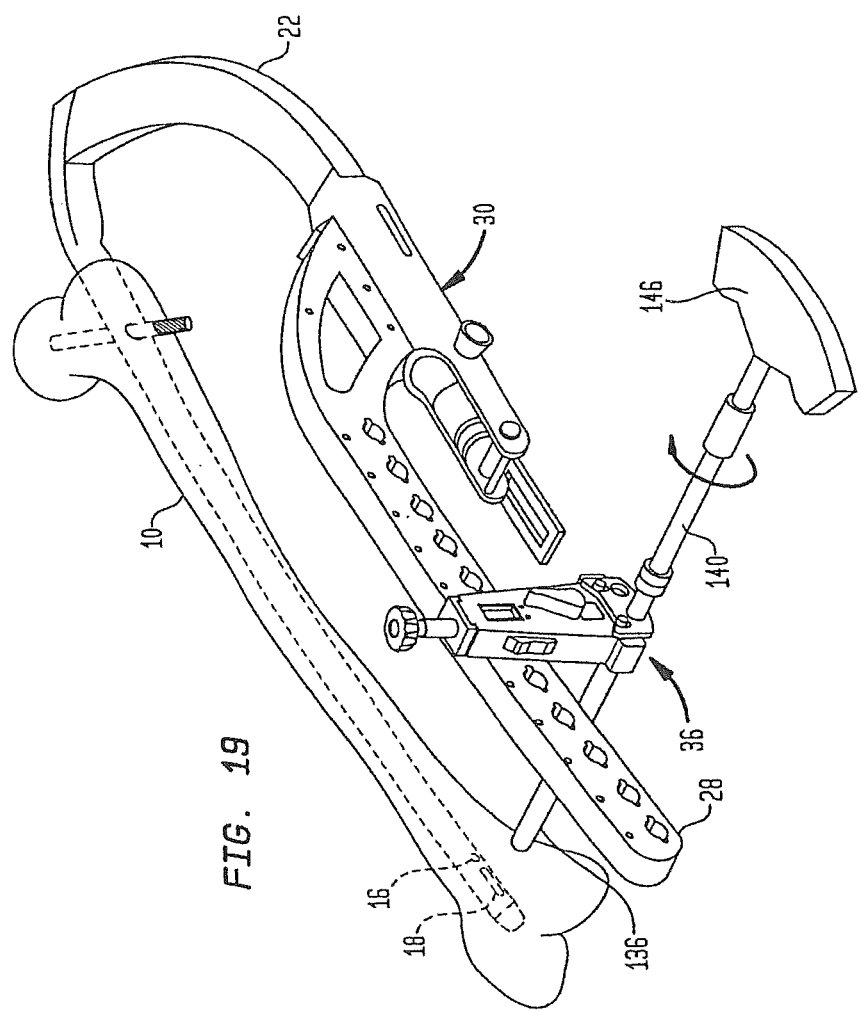
FIG. 19 shows the insertion of a bone screw through a drilled bone and into a cross bore of a bone nail utilizing the targeting apparatus and adjusting device of the present invention.

Referring to FIG. 19, there is shown the insertion of a first bone screw 136 through bore 80 of a left template and into the oblong cross bore 18 of bone nail 10. This of course is accomplished after cross bore 18 has been drilled in a similar manner as to that shown in FIG. 18.

Figure 20:
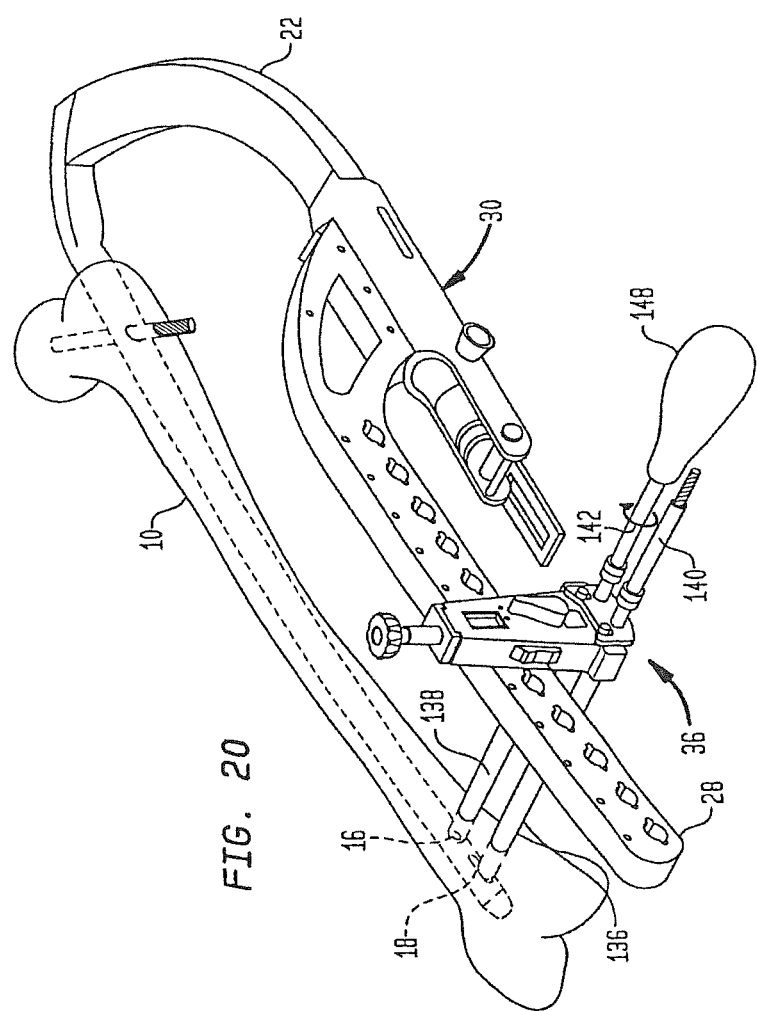
FIG. 20 is an isometric view showing the insertion of a second bone screw through a predrilled hole in the bone to a second cross bore of the bone nail.

Referring to FIG. 20, there is shown a second bone screw 138 being inserted through cross bore 16 of bone nail 10 in a manner similar to that of bone screw 136. Both bone screws are inserted with a standard screwdriver 140 and 142, respectively. For ease of use handle 146 of screwdriver 140 may be removed so that handle 148 of screwdriver 142 may be more accessible. Since two bone screws are being used, per FIG. 15 either static locking or secondary dynamization is being used (depending on which end of oblong bore 18 receives the screw).

Figure 21:
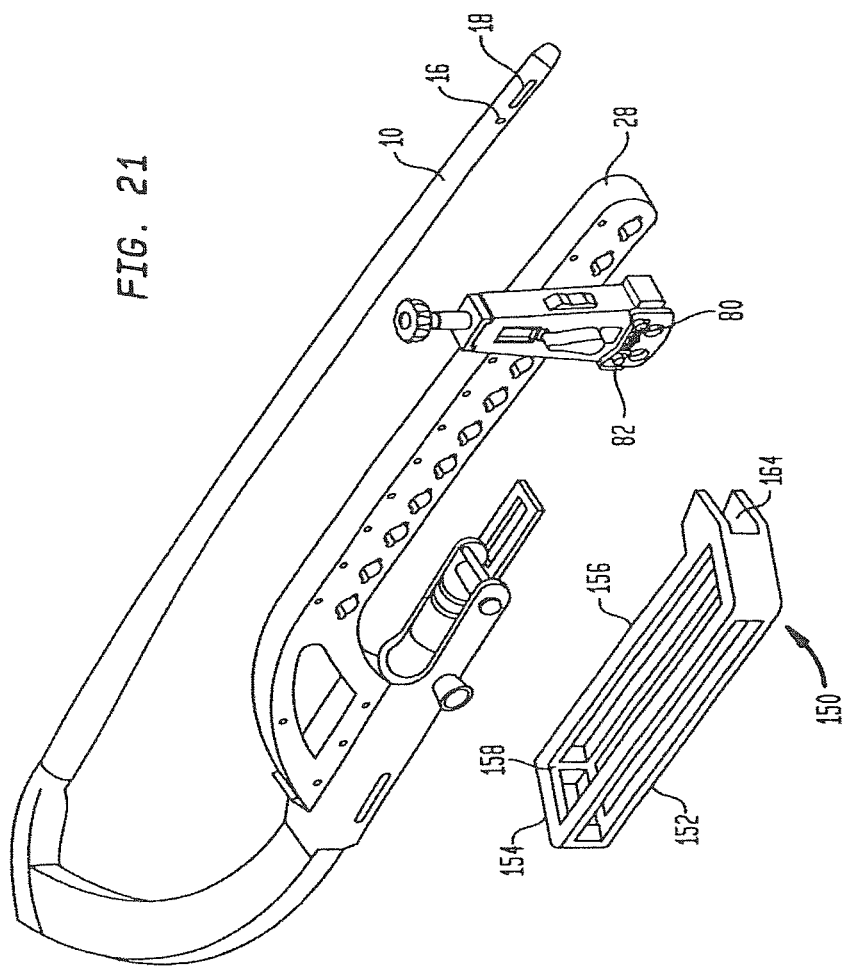
FIG. 21 shows the targeting apparatus of the present invention including a target indicator to be used with an oblique X-ray beam approach prior to the indicator being coupled to the adjusting device of the present invention.
Figure 22:
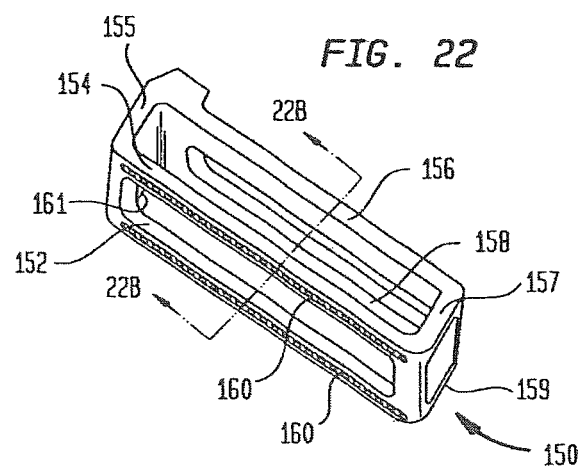
FIG. 22 is an isometric view of the target indicator showing a spaced pair of dashed radiopaque wires mounted in the same plane thereon.
Figure 22A:
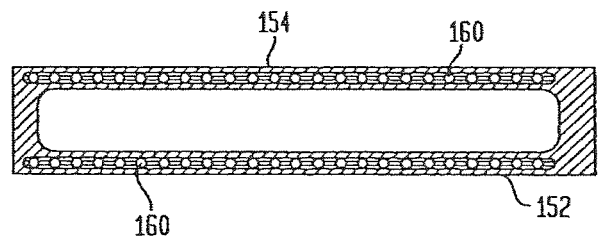
FIG. 22A is an elevation view of the target indicator showing the pair of dashed wires extending in the same vertical plane and parallel.
Figure 22B:
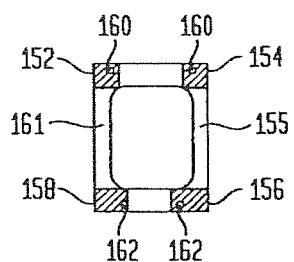
FIG. 22B is a cross-sectional view of the target indicator of FIG. 22A along line B-B rotated 90° showing the co-planar dash wires at the top and a pair of spaced solid radiopaque wires at the bottom.

FIGS. 21 through 29 show the use of the targeting apparatus 20 when used with the preferred oblique approach. The oblique approach is preferred because by orienting the x-ray beam at an angle of between 20° and 45° and preferably 30° to the longitudinal axis of bone nail 10, the actuation of screwdrivers 140, 142 via handles 146, 148 can take place by hand outside the x-ray beam. In order to align the adjusting device 36 and therefore holes 80, 82 with the bores 16 and 18 of the nail 10, a target indicator 150 is used. In the preferred embodiment, as shown in FIGS. 22, 22a, and 22b, indicator 150 is made of a predominantly radiolucent material such as PEEK and is in the shape of a parallelepiped. In the preferred embodiment a 30 degree angled parallelogram design was chosen for indicator 150 due to the operative technique. The angle of the indicator frame is canted 30 degrees from the perpendicular so that when the surgeon places the C-arm in angle of 40 or 20 degrees for anatomical reasons (sometimes the patient's other leg is in the way so the angle has to be rearranged) he or she sees none of the radiopaque markers. If a rectangular design (0 degrees from perpendicular) was used it would significantly "lose" usable radiopaque indicator length during the oblique alignment procedure. Indicator 15 has four legs 152, 154, 156, and 158, respectively. Legs 154 and 156 lie in a first plane parallel to a plane containing legs 152 and 158. Likewise, legs 152 and 154 are co-planer with a plane which is parallel to the plane containing legs 156 and 158. The legs 154 and 156 are connected by side legs 155 and 157 which, as described above, are angled at 30 degrees. Likewise legs 152 and 158 are connected by side legs 159 and 161. In the preferred embodiment, as can be seen in FIG. 22A legs 152 and 154, while being composed mainly of a radiolucent material, contain a radiopaque dashed or beaded wire 160. In the preferred embodiment the dashed or beaded wire 160 is molded into arms 152 and 154 during the manufacture of target indicator 150. As best seen in FIG. 22b legs 156 and 158 contain solid radiopaque wires 162 which are also preferably molded in place during manufacture of target indicator 150. As seen in FIG. 22b the spacing between solid wires 162 is less than the spacing between the dashed or beaded wires 160. Thus the different wires 160 and 162 can be easily distinguished in a fluoroscopic image showing two dashed lines and two solid lines. Of course the solid wires and dashed wires could be reversed without changing their function i.e. legs 156 and 158 could have the dashed wires 16 and legs 152 and 154 could have the solid wires.

In the preferred embodiment target indicator 150 has a dovetail-shape recess 164 best shown in FIG. 21 for engaging the male dovetail-shaped side extensions 90 and 92 of body 56 of adjusting device 36. Referring to FIG. 10 when the right femur is being addressed target indicator 150 is mounted on male dovetail extension 92 and when the left femur is addressed extension 90 is utilized for mounting target indicator 150. In both cases target indicator 150 extends from adjusting device 36 toward the proximal end of nail 10.

Referring to FIG. 23, there is shown targeting apparatus 20 mounted on a left femur with target indicator 150 mounted on dovetail 90 of adjusting device 36. The fluroscope machine 124 is shown as being oriented at an angle of about 30° to the longitudinal axis of nail 10. It can be seen that in this position the x-ray beam 170 is offset from the axis through which the bone screws are inserted into the distal femur and bores 16 and 18 and thus the hands of the surgeon would not enter the x-ray beam.

Figure 24:
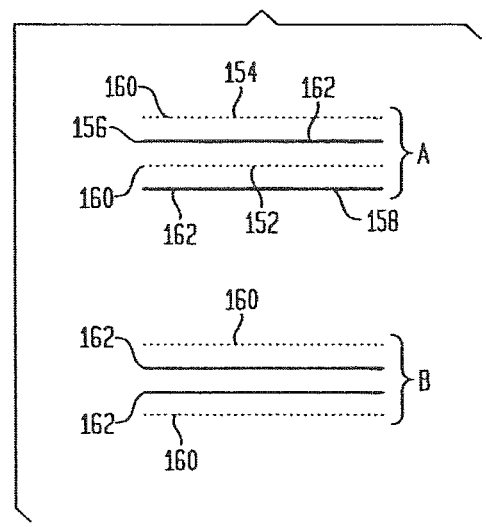
FIG. 24 shows in group A lines which would appear on a fluoroscope when the X-ray beam is not aligned with the X-Y plane of the nail cross bores and in Group B showing the dashed wire and solid wire alignment when the X-ray beam is correctly aligned.

Referring to FIG. 24, there is shown the alignment method for determining the correct location of the nail cross bores 16 and 18 using the target indicator 150. In the image group of four lines labeled "A" it can be seen that the dashed wire 160 in the upper leg 154 and lower leg 152 are positioned above and below the solid wire 162 of leg 156 with solid wire 162 of arm 158 located below both dashed wires 160. This means the x-ray beam is not coplanar with the x-y plane of the cross bores 16, 18 of nail 10. However, when proper alignment is achieved the grouping of lines shown in Group B of FIG. 24 now coincides with the correct alignment and spacing shown in FIG. 22b. Thus solid wires 162 are located between both dashed wires 160.

Figure 25:
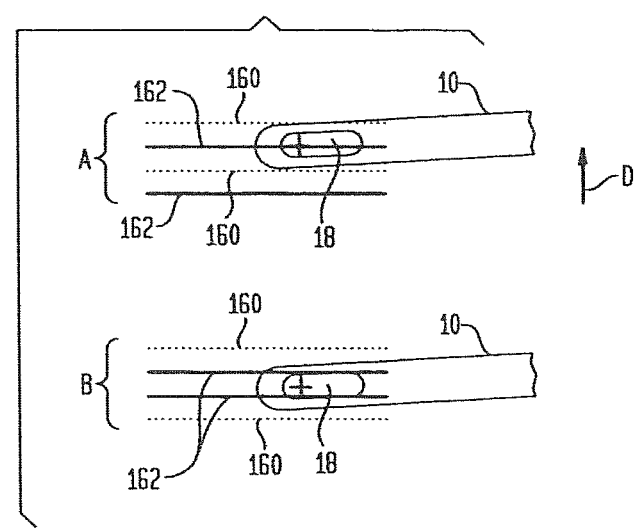
FIG. 25 shows the view on the fluoroscope when the center of the cross bore is incorrectly aligned (wire group A) and when the dashed and solid wires are correctly aligned about the center of the cross bore (Group B)
Figure 26:
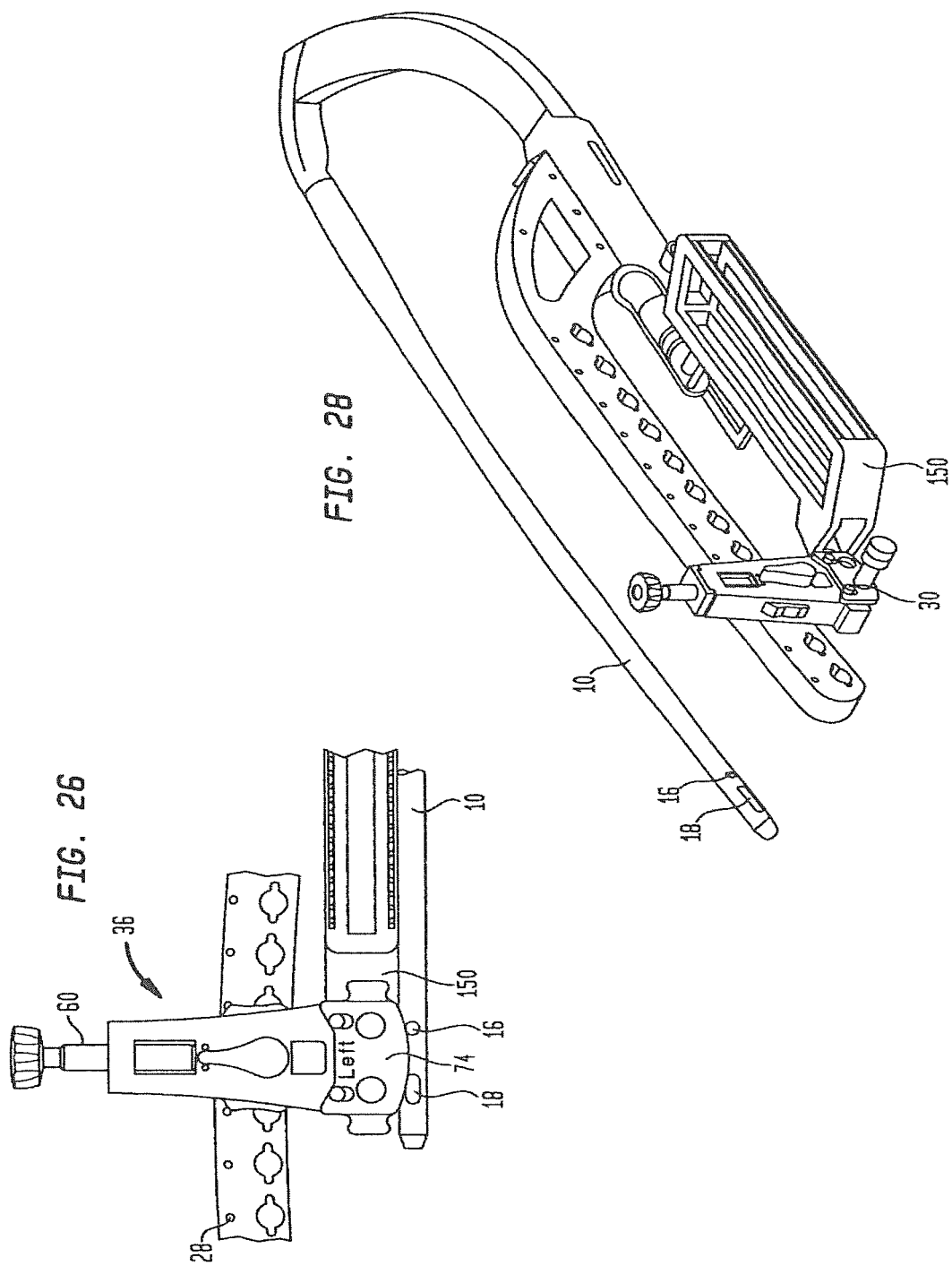
FIG. 26 shows a partial view of the targeting apparatus of the present invention including adjusting device with the target indicator mounted thereon being adjusted in the Z direction to correctly align the bores and the guide template with the cross bores in the bone nail.

Referring to FIG. 25, there is shown the use of adjusting device 36 and therefore target indicator 150 to locate the now aligned solid and dashed wires 160, 162 (group "B" of FIG. 24) with the center of the distal end of slotted or oblong opening 18 of nail 10. Group "A" of wires of 160, 162 show the incorrectly located center of cross bore 18 with Group "B" showing the correctly located center of cross bore 18. This is accomplished by adjusting screw 60 of adjusting device 36 in the direction of arrow "D" of FIG. 25. This process is shown for the left nail in FIG. 26 with the rotation arrows at the top of the figure indicating the turning of screw 60 to adjust the template 74 (in this case a left template 74) in the Z direction.

Figure 27:
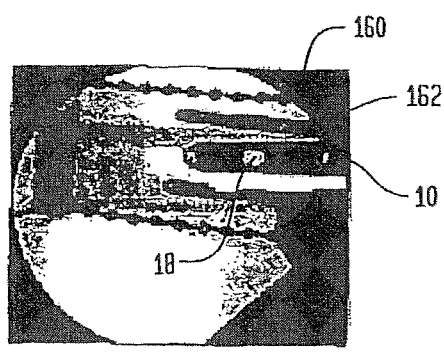
FIG. 27 is a fluoroscopic image of the correctly aligned target indicators with the dashed and solid wires correctly aligned with the cross bore in the bone nail.

Referring to FIG. 27, there is shown the fluoroscopic image viewed by the surgeon when the correct alignment as shown in FIG. 25 "B" is achieved. The bore 18 is located midway between solid wires 162 by use of adjusting screw 60.

Referring to FIG. 28, there is shown the tissue protection sleeve 114, 116 inserted through hole 80 of left template 74. The holes in the cortical bone are then drilled as discussed above with regard to the straight approach for both cross bore 18 and cross bore 16. Likewise the bone screws are inserted as shown in FIG. 29 in the same manner as accomplished with the straight approach.

The operative technique will now be described for using both the straight on and oblique approaches.

In the straight on approach after assembly of the targeting apparatus 20 and insertion of nail 10 the appropriate locking template 74 is brought over the template fixation pins 66, 68 and fixed by pushing the locking template down onto the pins.

Two different templates 74 are available. One for the static/static mode (right and left) and one for the static/dynamic mode. As described this can be accomplished by having template 44 used on one side the left nail and on the other side for the right nail.

The positioning pin 58 of the adjusting device is inserted in the bore 42 of arm 28 and is fixed by turning lever 71 clockwise.

The length of the required nail determines the position of adjusting device 36 on distal targeting arm 28. The nail lengths are preferably marked on the distal targeting arm above the appropriate hole 42.

The adjusting device is calibrated with the targeting device assembled to the nail prior to insertion into the bore canal.

This can be done on a table in the OR. The calibration places the adjusting device in the correct position for drilling cross bore 16, 18 with the nail in a non-deflected state. Thus once inserted the deflection will cause the bores 16, 18 to move only a small amount from the calibration position. The longer drill is assembled into the longer radiolucent tissue protection sleeve to insure the nail is reached.

The assembly is brought to proximal hole 16 first. Now the alignment is checked with a drill to see if the nail hole is hit directly without any resistance. The drill must go through the nail hole smooth and easily. If not, then the screw is turned until there is an easy and smooth access through the nail hole. When the proximal hole is calibrated then the calibration is repeated with the distal hole. This would be the correct medial-lateral position of adjusting device 36 if no bending occurs during insertion of the nail.

Calibration is done with the proximal nail hole first. This is done because it is not necessary for the adjusting device 36 to be exactly in the neutral position. This is because the proximal distal nail hole is likely to deflect less on nail insertion.

After the calibration is made, the tissue protection sleeve is withdrawn first followed by the drill sleeve and finally the drill. Then distal targeting arm coupling 30 can be released by moving lever 40 and fixation bolt 34 is removed. The distal targeting device assembly is detached and the fixation bolt may be put into a fixation bolt storage place molded on the distal targeting arm 28.

The adjusting device is not removed from the distal targeting arm to avoid misdrilling.

A straight approach may be used although not preferred. In this approach the x-ray beam is in line with bores 16 and 18 and perpendicular to the nail 10.

The distal targeting arm 28 with the adjustable device still assembled is coupled to the handle 22 via coupling device 30.

A radiolucent trocar 110 or 112 is assembled into the corresponding radiolucent tissue protection sleeve 114 or 116 and pushed through the distal locking hole 80 in template 74 on adjusting device 36 to the skin.

As shown in FIGS. 17A and 17B the x-ray view of the round and oblong distal holes are incorrectly aligned. FIG. 17C shows the x-ray beam correctly aligned in the Z plane.

Radiolucent trocar 110 or 112 is equipped with a radiopaque element 120 in tip 118 of the trocar. This radiopaque element can be used to determinate the exact position of the trocar tip in the straight approach.

This feature is used to provide an optimal lateral alignment of the tissue protection sleeves with the hole in the nail under X-ray control by turning the screw 40 of the adjusting device 36. When a proper medial-lateral (Z-plane) alignment is achieved, a radiopaque dot produced by element 120 is centered (see FIG. 17C) then the radiolucent trocar is replaced with a guide sleeve and standard metal trocar.

A small incision is started at the tip of the standard trocar, and is extended down to the lateral cortex of the distal femur. The trocar will typically extend back of the sleeve by approximately 3 mm when the tissue protection sleeve has reached the lateral cortex. The tissue protection sleeve should be in good contact to the bone (FIG. 6).

A second x-ray control should be performed to make sure that the alignment is still correct. If necessary an adjustment is performed by turning the knob of the adjusting device until a proper alignment is achieved.

The screw length can be determined by any known method. For example, the trocar is removed and replaced by calibrated 4.2 mm×340 mm drill. The surgeon drills through the first cortex and, as the second cortex is reached, reads off the measurement on a drill scale on the drill. The thickness of the cortex, which is approximately 5 mm, is added to this measurement to select the correct screw length.

Alternatively, the drill can be drilled through the second cortex and monitored by x-ray or fluoroscope image. The screw length can then be read directly from the scale on the drill.

The second cortex is then drilled. It is also possible to measure the correct screw length using a known screw gauge after drilling through the second cortex. The drill guide sleeve must be removed and the screw gauge may be advanced through the tissue protection sleeve. The small hook of the gauge is placed behind the medial cortex and the required locking screw length is read from the scale on the gauge.

The insertion of the screw is done in a standard manner as in the straight on approach as described above by use of a screwdriver through the tissue protection sleeve. The distal most hole is addressed first. Preferably a 5 mm locking screw is inserted through the distal end of radiolucent tissue protection sleeve by using the screwdriver until a mark on the screwdriver shaft approaches the distal radiolucent tissue protection sleeve 114 or 116. The screw head is advanced carefully until it is lightly in direct contact with the cortex.

When a mark on the screwdriver shaft reaches the tissue protection sleeve, this indicates that the screw head is near the cortex. Care should be taken not to overscrew. The screw head should come just into contact with the cortex and resistance should be felt.

Preferably, the screwdriver shaft is left inside the tissue protection sleeve. The screwdriver tip is left engaged in the first screw head and the tissue protection sleeve is pushed over the screw head, against the cortex. This helps ensure the stability of the system. The screwdriver shaft helps keep the targeting arm in position. Next, the most proximal hole is addressed.

Radiolucent trocar 110, 112 is assembled into the radiolucent tissue protection sleeve 114, 116 and pushed through the proximal locking hole in the adjusting device to the skin.

The same operative technique as described above for the most distal hole is followed and the distal screw length measurement is done in the same way as described above.

The drill sleeve is removed and the selected 5 mm fully threaded screw is inserted with the screwdriver.

The targeting device can now be removed by removing the screwdrivers/sleeves and opening lever 40 of the distal targeting arm. Fixation bolt 34 is then withdrawn.

In the preferred oblique approach as described above, the x-ray beam is oriented approximately 20° to 45° oblique to the distal locking sleeves and oblique to the nail. This offers the benefit, that during drilling, the drill tip can be seen but the image intensifier is not in the axis of the power tool and the drill.

After the calibration described above the distal targeting arm 28 with still assembled adjusting device 36 is pushed over the portion 26 of handle 20 until the spring detent is felt. In the alignment indicator window 38 the white line 39 on handle portion 26 can be seen. Fixation bolt 34 is then inserted into the bore until the click is felt and the targeting arm lever 40 is locked. The target indicator 150 is then attached over the proximal dovetail-shaped flutes 90, 92 (depending on right or left) of adjusting device 36.

The essential initial step in distal targeting with the oblique approach is to position the image intensifier approximately 20° to 45° and preferably 30° oblique to the distal locking sleeves and oblique to the nail.

To produce an optimal lateral alignment of the hole 16 or 18 in the nail under x-ray control, the c-arm of the x-ray machine is positioned in a way that the nail shaft is in the middle between the dashed wires and the solid wires of target indicator 150 as discussed above.

Now the adjustment is performed by turning knob 40 of adjusting device 36. A proper alignment is achieved when the locking hole is midway between the dashed and solid wires as shown in FIG. 27. The drilling and screw insertion is then performed as in the straight insertion as described above.

While in the oblique approach it is not necessary to use radiolucent trocars 110, 112. They could be used to further indicate the location of cross bores 16 or 18 in nail 10. The image on the fluoroscope would shown a line produced by radiopaque marker 12 rather than a circular dot as in the straight on approach.

Figure 30:
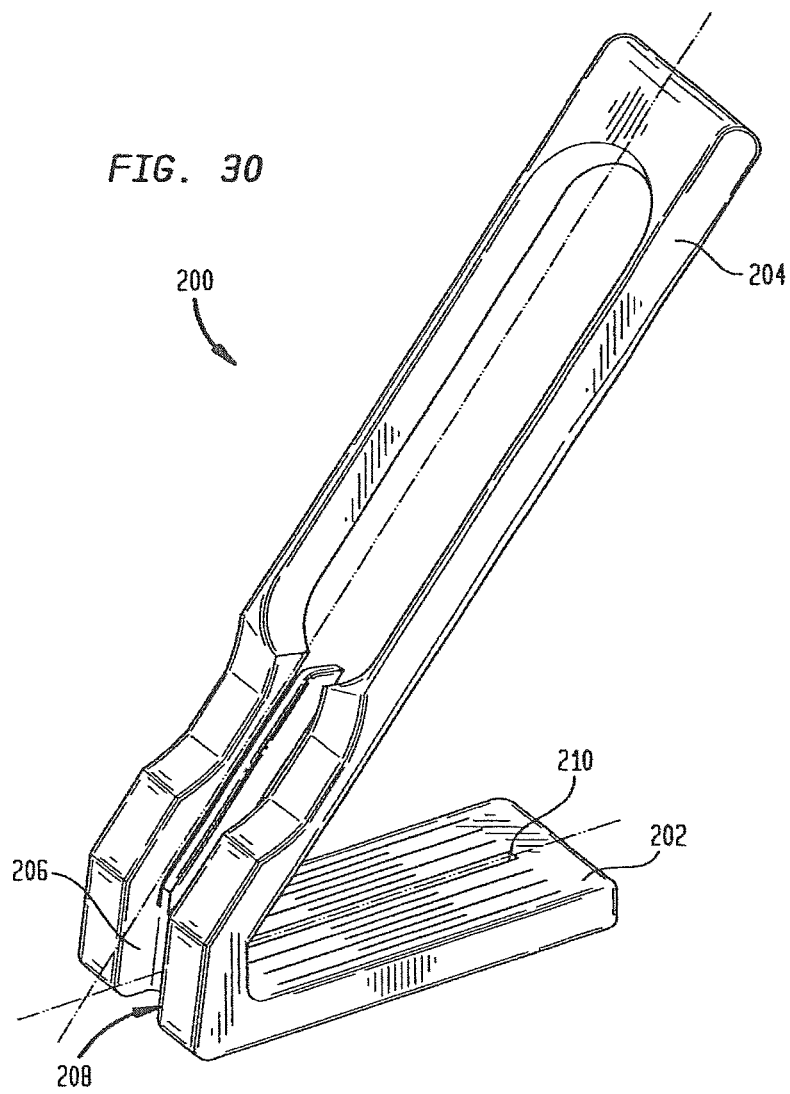
FIG. 30 is an isometric view of an alternate target indicator of the present invention having first and second legs oriented at an angle.
Figure 31:
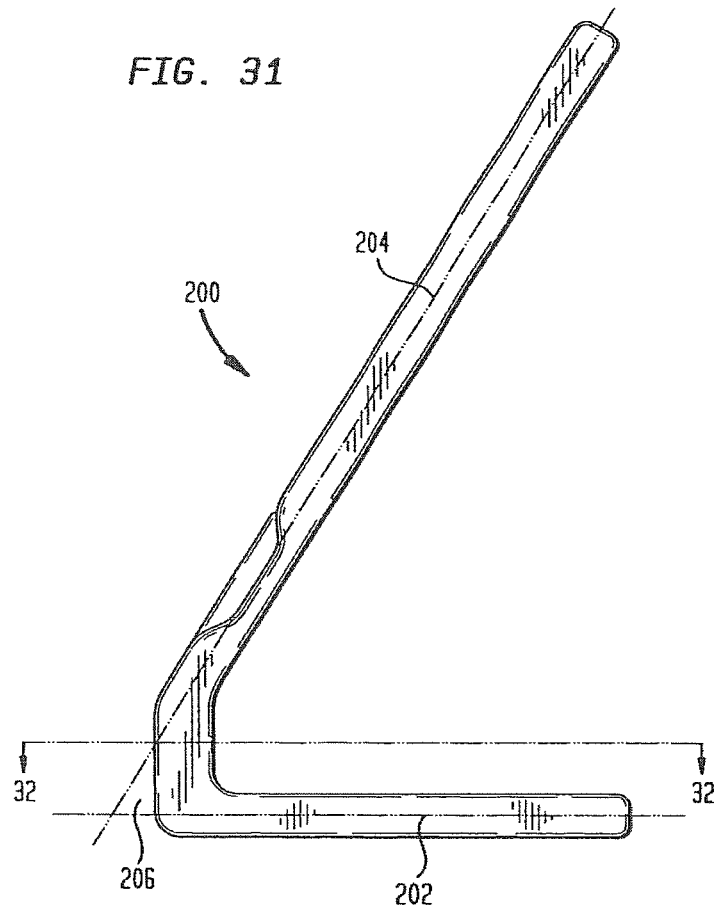
FIG. 31 is an elevation view of the target indicator of FIG. 30.

Referring to FIGS. 30 and 31 there is shown an alternate target indicator generally denoted as 200. Target indicator 200 includes a first leg 202 and a second leg 204. The legs are connected at an apex end 206. Target indicator 200 has a dove tail connection groove 208 for engaging dove tails 90, 92 of adjusting device 36. Target indicator 200 is preferably made mainly of a radiolucent material such as PEEK.

Figure 32:
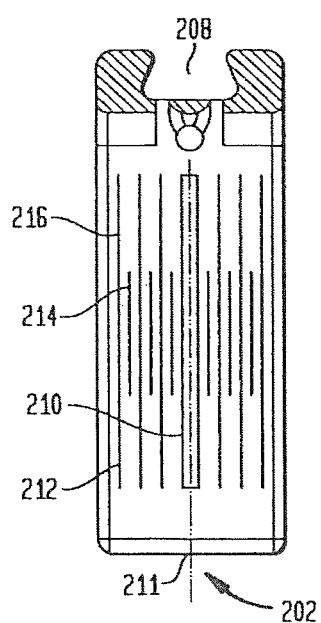
FIG. 32 is an elevation view of the first leg of the target indicator shown in FIG. 31 along lines 32-32 thereof.

Then referring to FIGS. 30-32 first arm 202 which is made of PEEK includes a series of radiopaque lines formed therein. In the preferred embodiment the central line 210 is a metal pin having a diameter greater than any of the other metal or radiopaque lines 212 which are formed on either side of the central line or pin 210.

Referring to FIG. 32 there is shown a top view of the first arm 202 including larger central rod 210 and a series of long and short thin radiopaque lines 212 having different lengths. The arm has a plurality of short length radiopaque lines or elements 214 and a series of longer radiopaque lines or elements 216. In the third embodiment there are three long and three short thin elements or lines 214, 216 on each side (above and below in FIG. 32) central pin 210. In the preferred embodiment the shorter lines 214 are spaced at 2.5 mm increments with respect to the center of the line of the pin 210 and with respect to the long lines 216. In a preferred embodiment lines 216 are spaced at 5 mm with one shorter line 214 located at 2.5 mm from each adjacent line 216. Thus, as shown in FIG. 32, the three long radiopaque elements or radiopaque lines 216 are spaced a maximum of 15 mm from a center line 211 of radiopaque pin 210. In the preferred embodiment the thin lines 214, 216 within the first leg 202 are formed by an etching process comparable to a method that is used in manufacturing circuit boards in the electronics industry. In the preferred embodiment the etched metal grid is then embedded into the radiolucent (plastic) material in a "sandwich" fashion. In the preferred embodiment the angle formed by the first and second legs at apex 206 is preferably 30°. This angle is chosen to keep the surgeon's hand out of the x-ray beam or fluoroscope during use. The angle between the first and second legs can vary between 15 and 60° and still allow the surgeon's hands to be outside of the x-ray beam during use.

Figure 33:
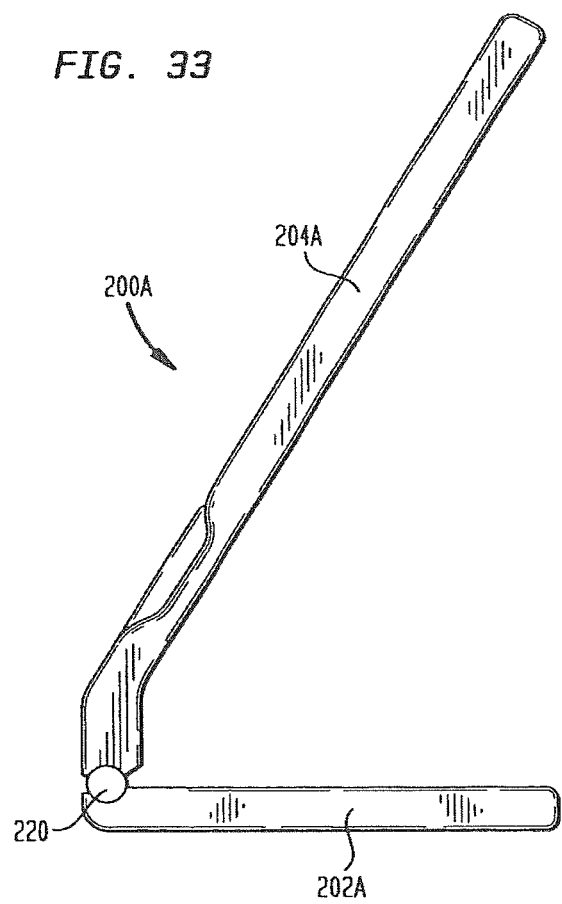
FIG. 33 is an elevation view of yet another embodiment of the target indicator of the present invention similar to that shown in FIG. 30 but with the first and second legs connected by a pivot hinge.

Referring to FIG. 33, there is shown a second embodiment of the target indicator shown in FIGS. 31-32. This target indicator includes a pivot pin 220 which allows first leg 202A to pivot with respect to second leg 204A to form an angle between 15° and 60°. A detent system (not shown) can be utilized to lock the desired angle between the first and second arms. The target indicator 200A is otherwise identical to that shown in FIGS. 30-32 and functions in an identical manner once the angle is set.

Figure 34:
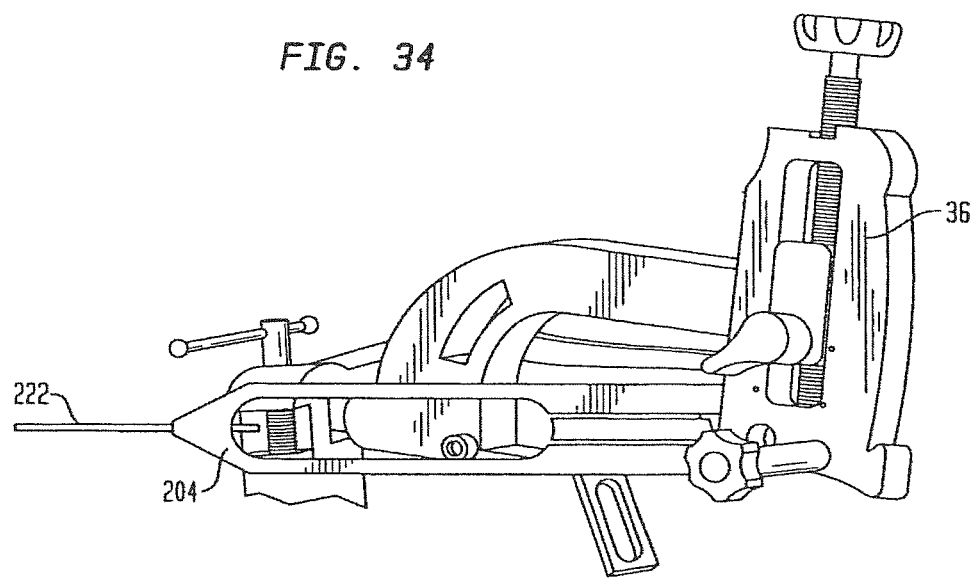
FIG. 34 is an isometric view of the target indicator of FIG. 30 mounted on an adjustment device similar to that shown in FIGS. 7-9.
Figure 35:
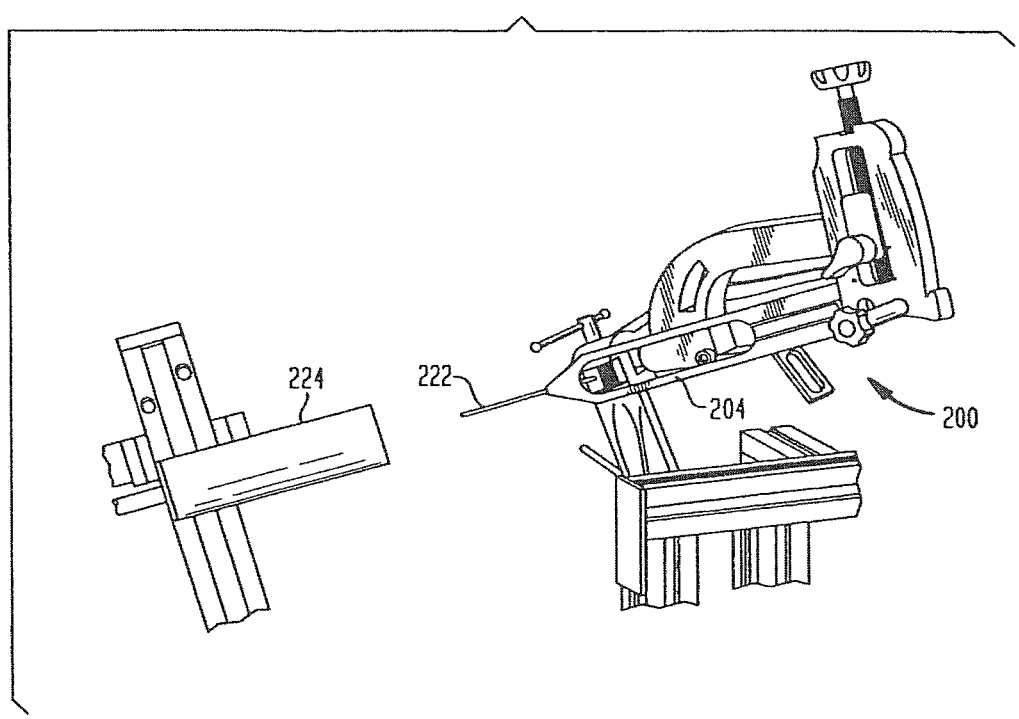
FIG. 35 is the targeting system of the present invention including the target indicator of FIG. 30 in a simulated x-ray beam.

Referring to FIG. 34 there is shown the targeting system of the present invention with the target indicator of FIGS. 30-34 mounted on an adjusting element 36 as described above with regard to target indicator 150. The target indicator is adjusted in an identical way with respect to the bores in the distal end of the implant, for example, a femoral nail. The only difference is that an alignment pin 222 is placed at the end of the second leg 204 so that it may be aligned with the beam of x-ray machine 224 shown in FIG. 35. The pin 222 appears as a dot when the beam is aligned with second leg 204.

The method for using the alternate and preferred target indicator is to attach the target indicator 200 to one of the two dovetail-shaped mounting elements 91, 92 on the adjusting device 36 (depending on whether it is mounted on a right or left femur). A metal trocar 240 is placed in the proximal hole of adjusting device 36, and k-wire or alignment pin 222 is inserted into the bore at the end of the alignment arm in order to adjust the C-arm of the x-ray machine. The trocar 240 may be housed within the tissue protection sleeve 130. The C-arm is aligned so that the x-ray beam is in line with the second leg 204 and at an oblique angle with respect to the nail 12. A first x-ray shot is taken, and the central thicker metal pin 210 shows the theoretical position of the tissue protection sleeve 130 housing the metal trocar.

Figure 36:
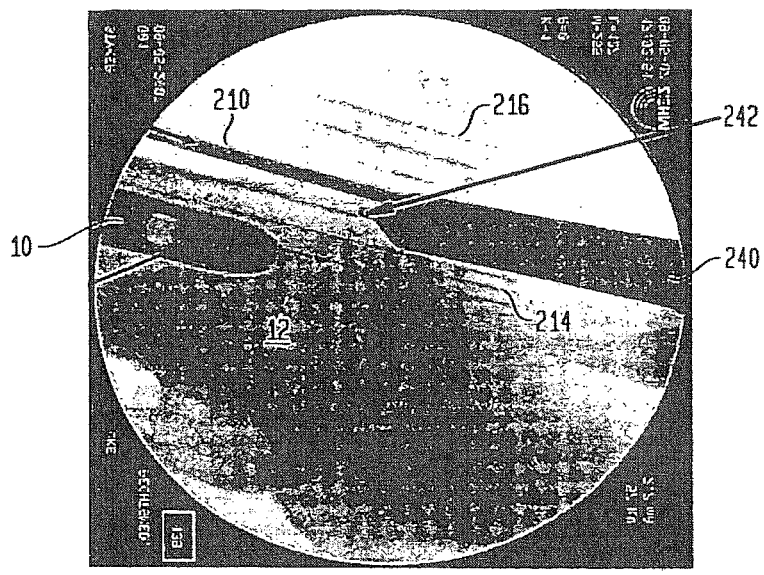
FIG. 36 is a fluoroscopic view of a trocar to be aligned with a distal hole in a nail utilizing the target indicating elements of FIG. 32.
Figure 37:
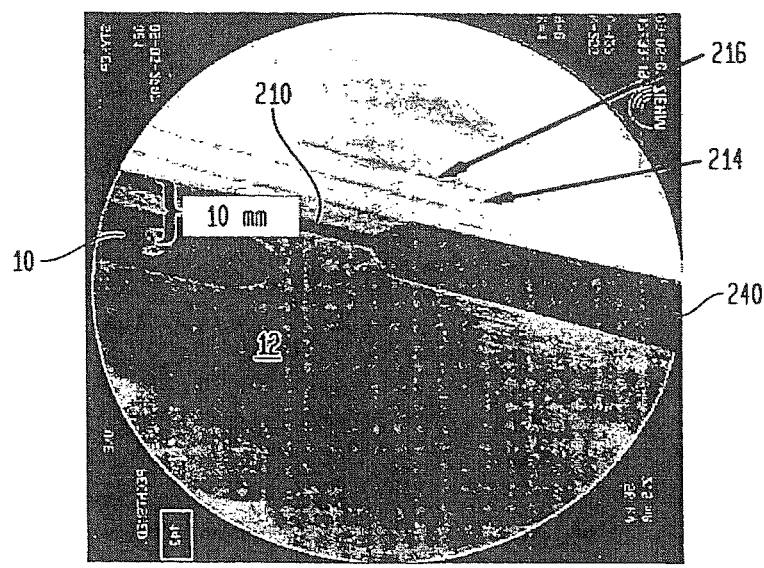
FIG. 37 is an intermediate fluoroscopic view of the trocar and nail being aligned.
Figure 38:
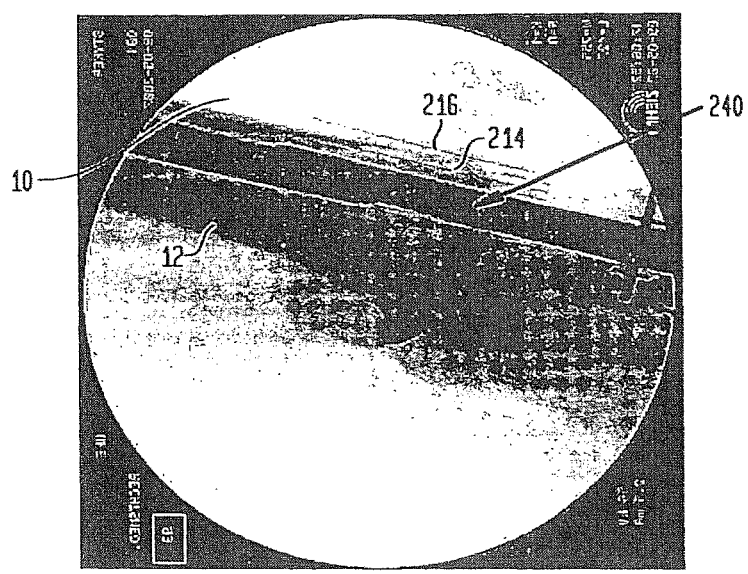
FIG. 38 is a fluoroscopic view showing the metal trocar in alignment with the distal nail hole of a bone nail.

FIG. 36 shows how a first x-ray could look with the pointed tip 242 of metal trocar 240 misaligned with the central thicker metal bar on the scale. The C-arm of the x-ray machine would have to be, again, aligned so that the metal tip of the trocar 240 lies in line with the thicker central metal pin 210. Such an alignment is shown in FIG. 37. There then exists a two-line (216) offset between the tip of the metal trocar and the central axis of the bore in the nail 12. Since the long lines 216 of the scale are spaced at 5 mm, the offset would be approximately 10 mm since the central axis of the distal nail hole is aligned with the second line below the axis of the thicker metal bar. As indicated above, the shorter etched lines 214 are spacer 2.5 mm, i.e., half-way between each pair of long lines 216. Obviously, other scale distances, either above and below the central thicker metal pin 210, are possible. These center-line offsets may result from the deformation of the bone nail during insertion. In any case, from the x-ray scan it can be seen whether the metal pin 210 is above or below the distal nail hole, and the distance between the two. The adjusting device 36 is adjusted to fully align the tissue protection sleeve and the trocar center with the distal nail hole (see FIG. 38). As shown in FIG. 38, the tissue protection sleeve 130 is fully aligned with the nail, and the drilling of the distal hole can begin. The hole is drilled in a conventional manner as described above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for locating a cross bore in an intramedullary nail comprising:
    inserting an intramedullary nail having a cross bore in a bone canal;
    coupling a targeting arm to the intramedullary nail, the targeting arm having a portion extending parallel to a longitudinal axis of the nail;
    mounting an adjusting device having a cross bore drill guide on the portion of the targeting arm extending parallel to the nail longitudinal axis, the adjusting device drill guide moveable in a direction perpendicular to a central axis of the cross bore and the nail longitudinal axis, the adjusting device having a target indicator coupled thereto having two sets of parallel radiopaque elements thereon;
    aligning the two sets of parallel radiopaque elements in an x-ray beam; and
    locating the cross bore in the nail by centering the cross bore in the x-ray beam between the two sets of parallel radiopaque elements if necessary by moving the adjusting device.

2. The method as set forth in claim 1 wherein a distance between a first set of parallel radiopaque elements is less than the distance between a second set.

3. The method as set forth in claim 1 wherein the first set of radiopaque elements are solid pins and the second set of radiopaque elements are a series of connected bead elements.

4. The method as set forth in claim 2 wherein the first set of radiopaque elements are solid pins and the second set of radiopaque elements are a series of connected bead elements.

5. The method as set forth in claim 2 wherein a plane containing ends of the radiopaque elements of the first and second sets of radiopaque element forms a non zero angle with a plane containing the first set of parallel radiopaque elements and a plane containing the second set of parallel radiopaque elements.

6. A method for locating a cross bore in an intramedullary nail comprising:
    inserting an intramedullary nail having a cross bore in a bone canal;
    coupling a targeting arm to the intramedullary nail, the targeting arm having a portion extending parallel to a longitudinal axis of the nail;
    mounting an adjusting device having a cross bore drill guide on the portion of the targeting arm extending parallel to the nail longitudinal axis, the adjusting device drill guide moveable in a direction perpendicular to a central axis of the bore and the nail longitudinal axis, the adjusting device having a target indicator coupled thereto having at least three parallel radiopaque elements thereon;

aligning the target indicator in an x-ray beam with the nail cross bore; and positioning the cross bore drill guide in alignment with the nail cross bore by aligning the drill guide in the x-ray beam with a central one of the parallel radiopaque elements, if necessary, by moving the adjusting device.

7. The method as set forth in claim 6 wherein the target indicator has first and second leg portions joined at an apex and angled with respect to one another at between 15 and 45°.

8. The method as set forth in claim 7 wherein the first leg portion has the at least three radiopaque elements therein.

9. The method as set forth in claim 8 wherein the second leg includes a radiopaque alignment element extending along a longitudinal axis thereof.

10. The method as set forth in claim 8 wherein the aligning of the target indicator in the x-ray beam comprises aligning the second leg radiopaque element coaxially with an axis of the x-ray beam.

11. The method as set forth in claim 6 wherein two of the at least three radiopaque elements are spaced from the central one of the radiopaque elements by between 2.5 and 5 mm.

12. The method as set forth in claim 11 wherein the adjusting device has indicators spaced at 2.5 to 5 mm corresponding to a target indicator first arm radiopaque element spacing.

13. A method for locating a cross bore in an intramedullary nail comprising:

inserting an intramedullary nail having an oblong cross bore with first and second portions in a bone canal;

coupling a radiolucent targeting arm to the intramedullary nail, the targeting arm having a portion extending parallel to a longitudinal axis of the nail;

mounting a partially radiolucent adjustment device having a cross bore drill guide on the portion of the targeting arm extending parallel to the nail longitudinal axis, the adjustment device having a radiopaque template thereon with a bore alignable with an end portion of a targeted oblong cross bore in a bone nail, the adjustment device adjustable in a direction perpendicular to a longitudinal axis of the cross bore and the bone nail longitudinal axis to align the bore of the radiopaque template of the adjustment device with one of the end portions of the targeted oblong cross bore, the adjusting device having a target indicator coupled thereto having at least two sets of two parallel radiopaque elements thereon;

aligning the two sets of two parallel radiopaque elements in an x-ray beam; and locating the cross bore in the nail by centering the cross bore in the x-ray beam between the two sets of parallel radiopaque elements if necessary by moving the adjusting device.

14. The method as set forth in claim 13 wherein a distance between a first set of parallel radiopaque elements is less than the distance between a second set.

15. The method as set forth in claim 13 wherein the first set of radiopaque elements are solid pins and the second set of radiopaque elements are a series of connected bead elements.

16. The method as set forth in claim 14 wherein the first set of radiopaque elements are solid pins and the second set of radiopaque elements are a series of connected bead elements.

17. The method as set forth in claim 14 wherein a plane containing ends of the radiopaque elements of the first and second sets of radiopaque element forms a non zero angle with a plane containing the first set of parallel radiopaque elements and a plane containing the second set of parallel radiopaque elements.

* * * * *